United States Patent [19]

Rorer

[11] Patent Number: 4,851,030
[45] Date of Patent: Jul. 25, 1989

[54] HERBICIDAL HETEROCYCLICMETHYLENEBENZENESULFONAMIDES

[75] Inventor: Morris P. Rorer, Newark, Del.

[73] Assignee: E. I. Du Pont de Nemours and Company, Wilmington, Del.

[21] Appl. No.: 939,427

[22] Filed: Dec. 8, 1986

Related U.S. Application Data

[63] Continuation-in-part of Ser. No. 723,997, Apr. 19, 1985, abandoned, which is a continuation-in-part of Ser. No. 618,730, Jun. 8, 1984, abandoned.

[51] Int. Cl.$^4$ .................... A01N 43/54; A01N 43/66; A01N 43/707; C07D 401/12
[52] U.S. Cl. .................................. 71/90; 71/92; 544/295; 544/296; 544/321; 544/324; 544/323; 544/331; 544/332; 544/182; 544/238; 544/216; 544/219; 544/312; 544/316; 544/310; 544/311; 544/319; 544/325

[58] Field of Search ............ 71/92, 90; 544/295, 544/296, 321, 324, 323, 331, 332, 182, 238, 216, 310, 311, 219, 319, 325, 312, 316

[56] References Cited

U.S. PATENT DOCUMENTS

| | | | |
|---|---|---|---|
| 4,586,952 | 5/1986 | Farnham | 71/92 |
| 4,602,936 | 7/1986 | Topfl et al. | 71/92 |
| 4,666,501 | 5/1987 | Hay et al. | 71/92 |
| 4,690,705 | 9/1987 | Christensen | 71/90 |

Primary Examiner—John M. Ford

[57] ABSTRACT

Novel benzenesulfonamide compounds containing an ortho-heterocyclicmethylene substituent such as N-[(4,6-dimethoxypyrimidin-2-yl)aminocarbonyl]-2-(5-methylthio-1,3,4-thiadiazol-2-ylmethyl)benzenesulfonamide are useful as preemergent and/or postemergent herbicides and/or plant growth regulants.

54 Claims, No Drawings

HERBICIDAL HETEROCYCLICMETHYLENEBENZENESULFONAMIDES

Background of the Invention

European patent application (EP-A) No. 44,209, published Jan. 20, 1982 discloses herbicidal compounds of formula

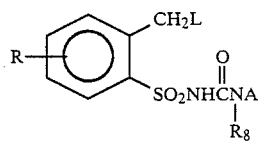

where L may be $CO_2R_{10}$, $CONR_3R_4$, CN, Cl, Br, $NR_3R_4$, $N^+R_3R_4R_{4'}$, $N(R_4)C(O)R_5$, $N(R_4)C(O)NHR_6$, $N(R_4)C(O)OR_7$, $S(O)_nR_7$, $OR_9$, $SO_2NR_3R_4$, OH, OC(O)$R_{11}$, OC(O)NHR$_{12}$ or OC(O)OR$_{13}$.

EP-A Nos. 83,975, published July 20, 1983, and 85,476, published Aug. 10, 1983, disclose herbicidal compounds of formula

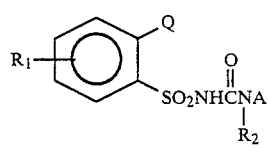

where Q is various 5- and 6-membered unsaturated, saturated and partially saturated heterocycles.

U.S. Pat. No. 4,370,480, issued Jan. 25, 1983, discloses herbicidal sulfonamides of formula

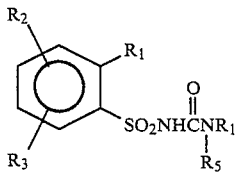      IV where $R_1$ may be

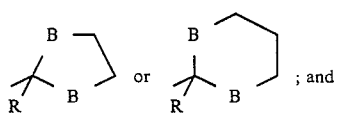  ; and

B is O or $S(O)_G$.

SUMMARY OF THE INVENTION

This invention relates to novel compounds of Formula I, suitable agricultural compositions containing them and their method-of-use as general and/or selective preemergence and/or postemergence herbicides and/or plant growth regulants.

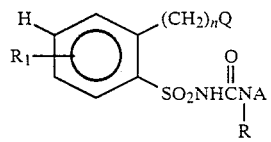      I wherein
R is H or $CH_3$;
$R_1$ is H, F, Cl, Br, $CH_3$, $CF_3$, $OCH_3$, $SCH_3$, $OCHF_2$ or $SCHF_2$;
n is 1 or 2;
Q is

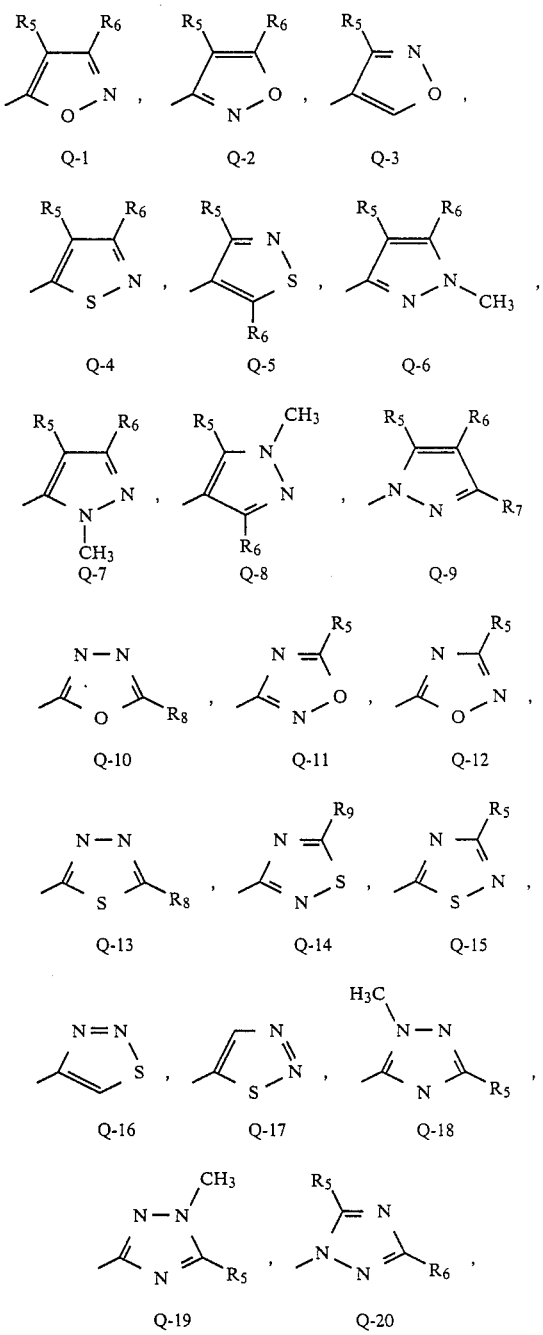

-continued

[Structures Q-21 through Q-54 shown]

Q-21, Q-22, Q-23, Q-24, Q-25, Q-26, Q-27, Q-28, Q-29, Q-30, Q-31, Q-32, Q-33, Q-34, Q-35, Q-36, Q-37, Q-38, Q-39, Q-40, Q-41, Q-42, Q-43, Q-44, Q-45, Q-46, Q-47, Q-48, Q-49, Q-50, Q-51, Q-52, Q-53, Q-54

$R_5$, $R_6$, $R_7$ and $R_{10}$ are independently H or $CH_3$;

$R_8$ is H, $CH_3$, $CH_2CH_3$, SH, $SCH_3$, $SCH_2CH_3$, $OCH_3$, $OCH_2CH_3$, $SCF_2H$, $SCH_2CH=CH_2$ or $SCH_2CN$;

$R_9$ is H or Cl;

$R_{11}$ and $R_{12}$ are independently H, $CH_3$ or $OCH_3$; and $R_{13}$ and $R_{14}$ are independently $CH_3$ or $OCH_3$;

A is

[Structures A-1 and A-2 shown]

A-1, A-2

-continued

A-3, A-4 structures

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;

Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$, $$\underset{R_2}{\overset{O}{\parallel}}R_2,\ -\underset{R_2}{\overset{L_1R_3}{\underset{L_2R_4}{C}}},$$

$$-\underset{R_2}{\overset{L_1}{\underset{L_2}{C}}}(CH_2)_m,\ \underset{L_2}{\overset{L_1}{CR_2}}\underset{L_2}{\overset{CH_3}{\diagdown}},\ OCF_2H,\ SCF_2H$$

or cyclopropyl;

m is 2 or 3;

$L_1$ and $L_2$ are independently O or S;

$R_2$ is H or $CH_3$;

$R_3$ and $R_4$ are independently $C_1$-$C_2$ alkyl;

Z is CH or N;

$Y_1$ is O or $CH_2$;

$X_1$ is $CH_3$, $OCH_3$, $OC_2H_5$ or $OCF_2H$; and $Y_2$ is H or $CH_3$; provided that (a) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(b) when X or Y is $OCF_2H$, then Z is CH; and (c) when Q is [structures shown], then A is A-4;

(d) when Q is Q-1, Q-2, Q-4, Q-5, Q-6, Q-8, Q-23, Q-24, Q-25, Q-26, Q-27, Q-28, Q-29, Q-45, Q-46, Q-47, Q-51, or Q-52 and A is A-1, then one of $R_5$ or $R_6$ is other than H;

(e) when Q is Q-10 or Q-13 and A is A-1, then $R_8$ is other than H, $CH_3$ or $CH_2CH_3$;

(f) when Q is Q-11, Q-12, Q-15 or Q-16, then A is A-2, A-3 or A-4;

(g) when Q is Q-14 and A is A-1, then $R_9$ is other than H;

(h) when Q is Q-3, Q-18 or Q-19 and A is A-1, then $R_5$ is $CH_3$;

(i) when Q is Q-31 or Q-33 and A is A-1, then one of $R_5$, $R_6$ or $R_7$ is other than H;

(j) when Q is Q-48 and A is A-1, then one of $R_5$, $R_{11}$ or $R_{12}$ is other than H;

(k) when Q is Q-49 or Q-50 and A is A-1, then one of $R_{11}$ or $R_{12}$ is other than H;

(l) when Q is Q-53 or Q-54 and A is A-1, then one of $R_{13}$ and $R_{14}$ is other than H; and their agriculturally suitable salts.

Preferred for reasons of greater ease of synthesis and/or greater herbicidal efficacy are:

(1) Compounds of Formula I wherein R is H.

(2) Compounds of Preferred 1 where Q is Q-1, Q-2, Q-3, Q-6, Q-7, Q-8, Q-9, Q-10, Q-11, Q-12, Q-13, Q-14, Q-15, Q-17, Q-20, Q-23, Q-24, Q-25, Q-26, Q-29, Q-30, Q-31, Q-32, Q-33, Q-34, Q-35, Q-36, Q-37, Q-38, Q-40, Q-41, Q-43, Q-44, Q-45, Q-46, Q-47, Q-48, Q-49, Q-50, Q-51, Q-52, Q-53, Q-54.

(3) Compounds of Preferred 2 where A is A-1 and Y is $CH_3$, $OCH_3$, $CH_2OCH_3$, $NHCH_3$, $CH_2CH_3$, $CH(OCH_3)_2$ or cyclopropyl.

(4) Compounds of Preferred 3 where $R_1$ is H, Cl, $CH_3$, $SCH_3$ or $OCH_3$ and X is $CH_3$, $OCH_3$, Cl, Br or $OCF_2H$.

(5) Compounds of Preferred 4 where n is 2.

(6) Compounds of Preferred 4 where Q is Q-1, Q-2 or Q-3.

(7) Compounds of Preferred 4 where Q is Q-6, Q-7, Q-8 or Q-9.

(8) Compounds of Preferred 4 where Q is Q-10, Q-11 or Q-12.

(9) Compounds of Preferred 4 where Q is Q-13, Q-14, Q-15, Q-17 or Q-20.

(10) Compounds of Preferred 4 where Q is Q-23, Q-24, Q-25, Q-26, Q-29 or Q-30.

(11) Compounds of Preferred 4 where Q is Q-31, Q-32, Q-33 or Q-34.

(12) Compounds of Preferred 4 where Q is Q-35, Q-36, Q-37 or Q-38.

(13) Compounds of Preferred 4 where Q is Q-40, Q-41, Q-43 or Q-44.

(14) Compounds of Preferred 4 where Q is Q-45, Q-46, Q-47, Q-48, Q-49, Q-50, Q-51, Q-52, Q-53 or Q-54.

An exemplary compound is: N-[(4,6-dimethoxypyrimidin-2-yl)aminocarbonyl]-2-(5-methylthio-1,3,4-thiadiazol-2-ylmethyl)benzenesulfonamide, m.p. 171°–175° C.

Detailed Description of the Invention Synthesis

The compounds of Formula I can be prepared by one or more of the methods described below in Equations 1, 2 and 3.

As shown in Equation 1 below, the compounds of Formula I can be prepared by treating sulfonamides of Formula II with the methyl ester of a pyrimidine or triazinecarbamic acid of Formula III in the prsence of an equimolar quantity of trimethylaluminum.

Equation 1

$$\text{II} + CH_3O\overset{O}{\overset{\parallel}{C}}N\underset{R}{-}A \xrightarrow{(CH_3)_3Al} I$$

wherein

A, R, $R_1$, Q and n are as previously defined.

The reaction of Equation 1 is best carried out at temperatures between 23° to 83° C. in an inert solvent such as methylene chloride or 1,2-dichloroethane for 12 to 96 hours under an inert atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride, ethyl acetate or diethyl ether or by chromatography procedures. The methyl carbamates, III, can be conveniently prepared by treatment of the corresponding heterocyclic amines of Formula VI with dimethyl carbonate or methyl chloroformate in the presence of a base such as sodium hydride or pyridine.

Further details of this reaction and the preparation of the carbamates of Formula III can be found in EP-A No. 83,975 (published July 20, 1983).

Alternatively, compounds of Formula I can be prepared by the reaction of sulfonamides of Formula II with the phenyl ester of the appropriate carbamic acid, IV, in the presence of an equimolar quantity of a tertiary amine base such as 1,8-diazabicyclo[5.4.0]-undec-7-ene (DBU).

Equation 2

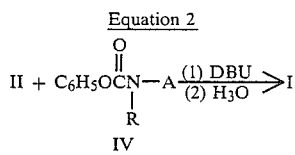

wherein

A and R are as previously defined.

The reaction of Equation 2 is best carried out at 20° to 30° C. in an inert solvent such as dioxane or acetonitrile. Aqueous acid work-up affords the desired products, according to the teachings of EP-A No. 70,804 (published Jan. 26, 1983) and South African patent applications 825,042 and 830,441. The phenyl carbamates, IV, can be prepared by treating the corresponding heterocyclic amines of Formula VI with diphenyl carbonate or phenyl chloroformate in the presence of a base such as sodium hydride or pyridine.

Also, many compounds of Formula I can be prepared by reacting an appropriate sulfonyl isocyanate, V, with the appropriately substituted aminoheterocycle, VI, as shown in Equation 3 below.

Equation 3

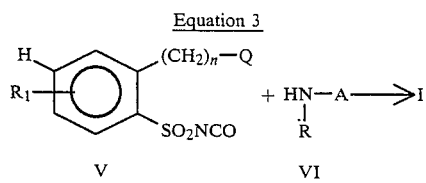

wherein

R, $R_1$, A and n are as previously defined; and

Q is Q-1 to Q-5, Q-10 to Q-17, Q-23 to Q-28, and Q-31 to Q-34.

The reaction is best performed in an inert solvent such as methylene chloride, tetrahydrofuran, acetonitrile or toluene at 23° to 100° C. for 1 to 24 hours. In cases where the products are insoluble in the reaction solvent, they may be isolated by simple filtration. When the products are soluble, they may be isolated by evaporation of the solvent and trituration of the residue with an appropriate solvent such as 1-chlorobutane, diethyl ether, methanol or ethyl acetate and filtration. The products may be further purified by column chromatography procedures.

Sulfonyl isocyanates of Formula V above may be prepared, although often times in low yields, from corresponding sulfonamides of Formula II by methods analogous to those described in U.S. Pat. No. 4,238,621 and EP-A No. 83,975 (published July 20, 1983). By a preferred method, sulfonamides are reacted with phosgene, in the presence of n-butyl isocyanate and a tertiary amine catalyst, at reflux in an inert solvent such as xylenes. A preferred catalyst is 1,4-diazabicyclo[2.2.2]octane (DABCO). Alternatively, isocyanates, V, may be prepared by (1) reacting sulfonamides, II, with n-butyl isocyanate and a base such as potassium carbonate at reflux in an inert solvent such as 2-butanone to form a n-butyl sulfonylurea; and (2) reacting this compound with phosgene and DABCO catalyst at reflux in xylenes solvent.

Many sulfonamides of Formula II can be prepared by the sequence of reactions shown below in Equation 4.

Equation 4

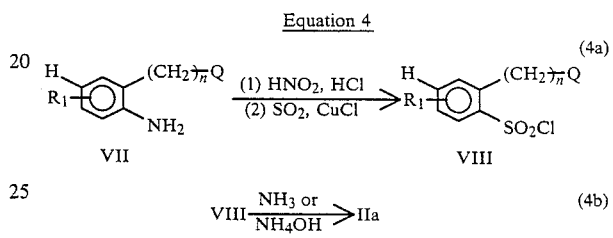

wherein $R_1$ and n are as previously defined; and

Q is Q-1 to Q-34 and Q-45 to Q-54.

The reactions of Equation 4(a,b) can be run by methods analogous to those described in EP-A Nos. 83,975 (published July 20, 1983) and 85,476 (published Aug. 10, 1983). In Reaction 4(a) the methods require reacting amines of Formula VII with sodium nitrite in concentrated hydrochloric acid and acetic acid to form diazonium salts. Following addition and reaction of the diazonium salt suspensions with suspensions containing excess sulfur dioxide and copper (I) chloride or copper (II) chloride catalyst in acetic acid solvent, the sulfonyl chlorides, VIII, are isolated by addition of water, filtration if VIII is a solid, or extraction with methylene chloride if VIII is an oil. Generally, the sulfonyl chlorides, VIII, are pure enough to carry on to the next step without further purification.

In Reaction 4(b), sulfonamides, IIa, are prepared by reacting sulfonyl chlorides, VIII, with excess ammonia or aqueous ammonium hydroxide in an inert solvent such as tetrahydrofuran. Sulfonamides, IIa, are isolated by filtration and washing with water to remove the by-product ammonium chloride, and concentrating the organic solution. The sulfonamides may be further purified by recrystallization or chromatography procedures.

Many sulfonyl chlorides of Formula VIII may also be prepared via oxidative chlorination of the appropriate thioethers of Formula A, as illustrated in Equation 4a.

Equation 4a

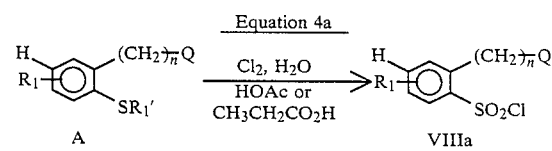

wherein $R_1$ and Q do not contain a thioether or alkenyl group;

$R_1'$ is $C_2$-$C_3$ alkyl or benzyl; and

Q is Q-1 to Q-34.

The reaction of Equation 4a may be carried out by contacting a suspension of the thioether A in a solvent such as acetic acid or propionic acid in the presence of at least 2.5 equivalents of water with at least 3.0 equivalents of chlorine at about $-10°$ to $30°$ C. for 0.25 to 5 hours. The reaction is poured into ice-water and the product is isolated by filtration or extraction with a solvent such as methylene chloride. The extract is optionally washed with aqueous sodium bicarbonate until neutral or slightly basic, then dried, and the solvent is evaporated to yield a product generally pure enough to be carried directly to the next step. Thioethers, A, may be prepared by analogy with methods described hereinafter in Equation 11a, or simple modifications thereof, from appropriate corresponding thioethers containing ortho-functional groups, J, by those skilled in the art.

Certain sulfonamides of Formula II are preferably prepared from appropriately substituted o-(methoxycarbonyl)alkanebenzenesulfonamides of Formula IX, as shown below in Equation 5.

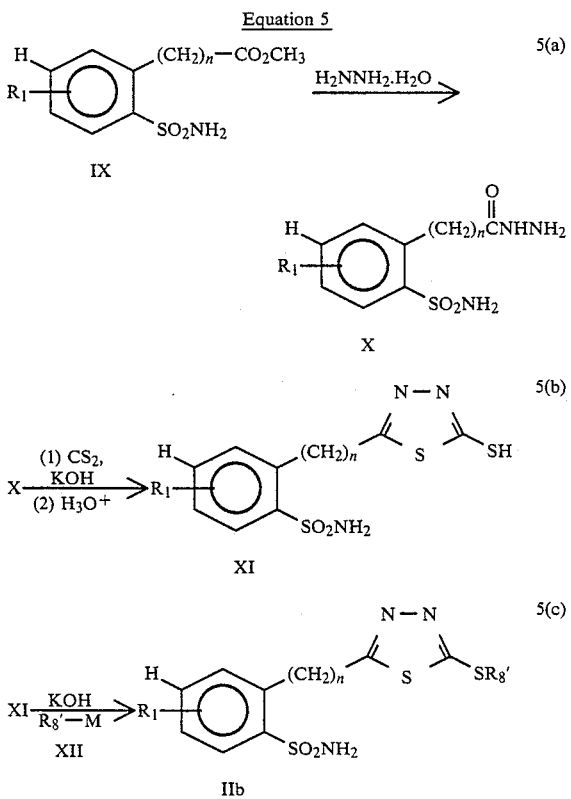

wherein
  $R_1$ is as previously defined;
  $R_8'$ is $CH_3$, $C_2H_5$, $CF_2H$, $CH_2CH=CH_2$ or $CH_2CN$; and
  M is Cl, Br or I; and n is 1.

Reaction 5(a)

The conversion of carboxylic esters to hydrazides is well known in the literature. In a typical procedure, a carboxylic ester of Formula IX is reacted with an excess of hydrazine monohydrate (preferably 10 to 30% mole excess) in an inert solvent such as methanol or ethanol at reflux for one to 24 hours. The hydrazides, X, are isolated by filtration or by concentration to remove the solvent and triturating the hydrazide residue, X, with water. The compounds are generally sufficiently pure to be carried on directly to step 5(b), but may be purified further by recrystallization procedures.

Reaction 5(b)

The conversion of hydrazides to 2-mercaptooxadiazoles is also well known in the literature, e.g., R. W. Young and K. H. Wood, J. Am. Chem. Soc., 77, 400 (1955). In a typical procedure, hydrazides, X, are heated at reflux with equimolar amounts of potassium hydroxide and an excess of carbon disulfide in methanol or ethanol solvent until the evolution of hydrogen sulfide has nearly stopped. By these conditions, however, thiadiazole XI is obtained from hydrazide X, based on mass spectrum analysis. Thiadiazoles, XI, are isolated by concentration of the solvent, addition of water to the residue, filtration of the aqueous suspension to remove insoluble impurities, acidification of the aqueous filtrate with hydrochloric acid and filtration. Compounds, XI, are generally pure enough to carry on to step 5(c), but may be further purified by recrystallization procedures.

Reaction 5(c)

Thiadiazoles, XI, are alkylated by reaction with an equimolar amount of base such as potassium hydroxide and excess alkylating agent, XII, at reflux in an inert solvent such as methanol or ethanol for 0.5 to 24 hours. Sulfonamides, IIb, are isolated by concentration of the solvent, addition of water to the residue and filtration. For the case where $R_8'=CF_2H$, the reaction is preferably run in N,N-dimethylformamide (DMF) solvent at $60°-90°$ C. with excess potassium carbonate as base. Following addition of water, sulfonamides, IIb, are isolated by filtration; they may be purified by recrystallization procedures. Esters of the general Formula IX, where n is 1, are known; see U.S. Pat. No. 4,348,219 (issued Sept. 7, 1982).

Sulfonamides of Formula II containing an o-methanepyridinyl, -pyrimidinyl, -pyrazinyl, -pyridazinyl or -triazinyl group (Q is Q-45 to Q-54) may be prepared by the sequence of reactions shown below in Equation 6.

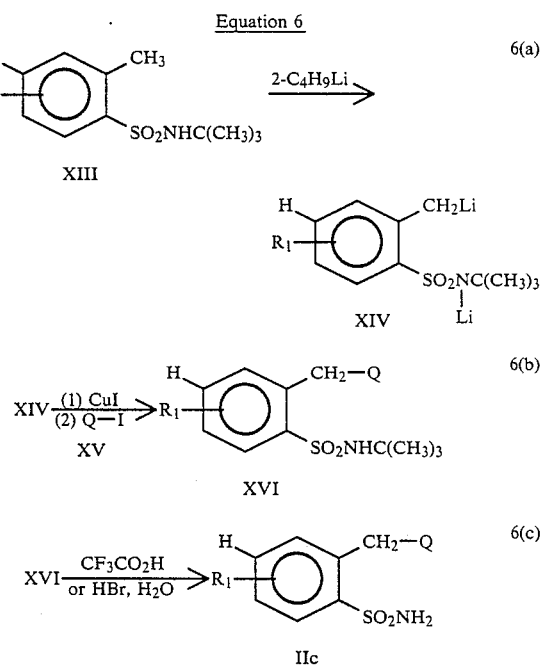

wherein
R₁ is as originally defined, except R₁ may not be Br; and
Q is Q-45 to Q-54.

The compounds of Formula IIc are prepared by analogy with the teachings of EP-A No. 85,476 (published Aug. 10, 1983).

Reactions 6(a,b)

An N-t-butyl sulfonamide of Formula XIII is dissolved in an ethereal solvent, such as tetrahydrofuran, and two equivalents of n-butyllithium in hexane are added at about −70° C. After 1-5 hours at about −70° C., the compound of Formula XIV is formed. This is not isolated, but one equivalent of a copper(I) iodide salt is added at about −70°, followed by 1-1.5 equivalents of an appropriately substituted heteroaromatic iodide of Formula XV. The reaction mixture is heated at 0° to 70° C. for 1-3 days, concentrated and poured onto aqueous ammonia. Compounds of Formula XVI are isolated by filtration if solids or by extraction with methylene chloride and concentration if oils. The compounds, XVI, may be further purified by recrystallization or chromatography procedures.

The compounds of Formula XV above may be prepared according to methods known in the art, such as those reviewed in "The Chemistry of Heterocyclic Compounds", a series published by Interscience Publ., New York and London, the teachings of which are incorporated herein by reference. The iodopyridines are described in Vol. 14 of the above series, pp. 407-488. Iodopyrimidines are described by D. J. Brown and S. F. Mason in Vol. 16 of the above series. The preparation of iodopyrazines is taught by A. Hirshberg and P. E. Spoerri, *J. Orq. Chem.*, 26, 1907 (1981) and iodopyridazines are described by D. L. Aldons and R. N. Castle in Vol. 28 of the Interscience series, pp. 240-241. The iodo-1,3,5-triazines are described by E. M. Smolin and L. Rapoport, in Vol. 13 of the above series, and a method for preparing iodo-1,2,4-triazines is taught by A. Rykowski and H. C. van der Plas, in *J. Orq. Chem.*, 45, 881 (1980).

Reaction 6(c)

This reaction is conducted by heating a compound of Formula XVI with 2-10 equivalents of trifluoroacetic acid or aqueous HBr with or without an inert solvent at 30°-70° for 1-3 days. The product, IIc, may be isolated as a trifluoroacetate or hydrobromide salt by evaporation of solvent and excess acid and trituration with ether. The free base may be obtained by neutralization of the salt with aqueous base, extraction into an organic solvent, and concentration of the organic extracts. Products, IIc, may be further purified by recrystallization or chromatography procedures.

As shown in Equation 7 below, sulfonamides of Formula IIe containing a tetrahydrofuran or tetrahydrothiophen group (Q is Q-35 to Q-38) may be prepared by catalytic reduction of the corresponding furan or thiophene groups of sulfonamides of Formula IId (Q' is Q-31 to Q-34).

Equation 7

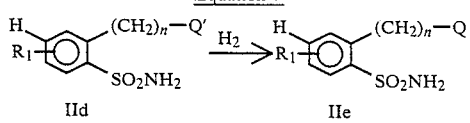

wherein

R₁ and n are as originally defined;
Q' is Q-31 to Q-34; and
Q is Q-35 to Q-38.

Selective reductions of the type shown in Equation 7 are well known in the literature. The choice of catalyst, solvent, pressure and temperature for reduction of furans has been reviewed by Samuel Sevadesh in "The Furans" by A. P. Dunlop and F. N. Peters, Reinhold Publishing Corporation, New York, N.Y. 1953, pp. 674-713; and by P. N. Rylander in "Catalytic Hydrogenation in Organic Synthesis", Academic Press, 1979, pp. 227-234. The reduction of thiophenes is reviewed by H. D. Hartough in "Thiophene and Its Derivatives", The Chemistry of Heterocyclic Compounds Series, Interscience Publishers, Inc., New York, N.Y. 1952, pp. 167-169. Sulfonamides of Formula IId above are prepared from appropriate anilines by the sequence of reactions described above in Equation 4.

Equation 8 below illustrates a method for preparing sulfonamides of Formula IIf containing acetal or thioacetal groups (Q is Q-39 to Q-44).

Equation 8

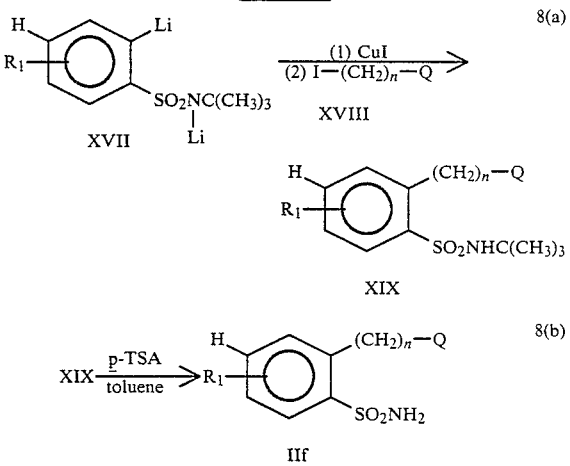

wherein

R₁ is as originally defined except R₁ is other than Br or CH₃;
n is as originally defined; and
Q is Q-39 to Q-44.

Reaction 8(a)

The compounds of Formula IIf are prepared by analogy with the teachings of J. G. Lombardino, *J. Orq. Chem.*, 36, 1843 and EP-A No. 85,476.

An appropriate N-t-butyl sulfonamide dissolved in tetrahydrofuran solvent is reacted with two equivalents of n-butyllithium in hexane at 0° to 25° C. for 1-5 hours to form dilithio salts XVII. One equivalent of copper(I) iodide is then added at −20° to 0° C., followed by 1-1.5 equivalents of an appropriate iodoalkylacetal or thioacetal of Formula XVIII. The reaction mixture is heated at 0° to 70° C. for 1-3 days, then worked up analogous to that described for Reaction 6(b) above to give compounds of Formula XIX.

Reaction 8(b)

In this step the tert-butyl group is removed from XIX by heating these compounds in toluene in the presence of a catalytic amount of p-toluenesulfonic acid (p-TSA). The products, IIf, are isolated and purified by stripping the solvent, followed by recrystallization or chromatography procedures on the crude residues.

The anilines of Formula VII in Equation 4 above can be prepared by reduction of corresponding nitrobenzenes of Formula XX, as illustrated in Equation 9 below Equation 9

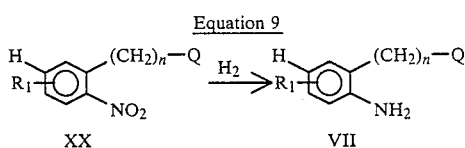

wherein
R₁ is as originally defined; and
Q is Q-1 to Q-34 and Q-45 to Q-54.

The reduction reactions of Equation 9 can be run by methods known in the literature by those skilled in the art. For details see, for example, EP-A Nos. 83,975 and 85,476 and references cited therein.

The nitrobenzenes of Formula XX above, containing an o-alkaneheterocyclic group, are important intermediates for the preparation of many of the compounds of this invention. They can be prepared by those skilled in the art by the applicatiion of appropriate methods selected from the variety of known literature procedures for preparing substituted aromatic heterocycles.

For example, nitrobenzenes of Formula XXa, containing an o-alkylfuran or -thiophene group (Q is Q-31 to Q-34), can be prepared by analogy with the teachings in EP-A No. 85,476, and references cited therein, as illustrated in Equation 10 below.

Equation 10

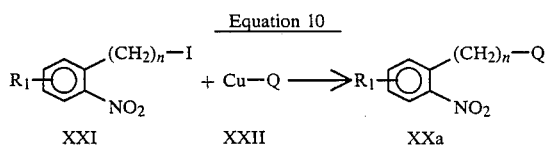

wherein
R₁ and n are as originally defined; and
Q is Q-31 to Q-34.

Thus, a furyl- or thienylcopper compound of Formula XXII is reacted with an o-(iodoalkyl)nitrobenzene of Formula XXI in an inert solvent such as pyridine or quinoline at 0° to 60° C. for 1-3 days. The product, XXa, is isolated by addition of an acid such as acetic acid and water, extraction with methylene chloride, stripping of solvent and chromatographing the crude product. The copper compounds of Formula XXII are prepared by reacting the corresponding lithium compounds with cuprous iodide or cuprous bromide in an inert solvent such as ethyl ether. The detailed procedures for analogous types of reactions are described in the following references: M. Nilsson and C. Ullenius, *Acta. Chem. Scand.*, 24, 2379-2388 (1970); C. Ullenius, *Acta. Chem. Scand.*, 26, 3383-3386 (1972).

Nitrobenzenes of Formula XX containing an o-ethanepyrazinyl group (Q is Q-51) can be prepared by analogy with the teachings of J. Behun and R. Levine, *J. Org. Chem.*, 26, 3379 (1961). The method requires heating methylpyrazine with potassium hydroxide in the presence of excess amounts of an o-nitrobenzyl alcohol.

Nitrobenzenes of Formula XX, containing an o-ethanepyridyl group (Q is Q-45 to Q-47), can be prepared by reacting o-nitrobenzyl chlorides or bromides with methylpyridines in the presence of sodamide in liquid ammonia. For details, refer to review publications for this type of reaction, i.e., Bergstrom and Fernelius, *Chem. Rev.*, 20, 413 (1937); Bergstrom, ibid. 35, 77 (1944) and Levine and Fernelius, ibid, 54, 449 (1954); also see for general description of this type of reaction, "Pyridine and Its Derivatives", Vol. 14, Part, 2. pp. 169-170, of the series "The Chemistry of Heterocyclic Compounds", A. Weissberger, Ed.

Nitrobenzenes of Formula XX containing an o-ethanepyrimidin-2-yl group (Q is Q-48) can be prepared by heating a 1-(o-nitrophenyl)-2-amidinylethane hydrochloride salt with 1,1,1,3-tetramethoxypropane in an inert solvent such as ethanol, a method well known in the art for preparing 2-(alkyl)substituted pyrimidines.

Many of the nitrobenzenes of Formula XX can be prepared by analogy with methods described in EP-A No. 83,975 and references cited therein, as illustrated in Equation 11 below.

Equation 11.

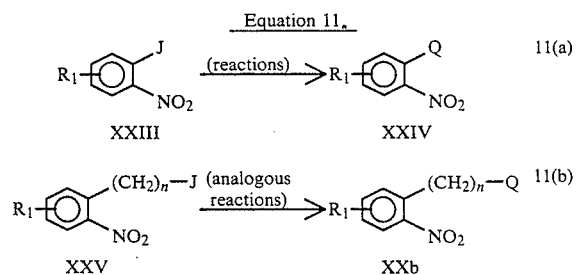

wherein
R₁ and n are as originally defined;
Q is Q-1 to Q-30; and
J are appropriate functional groups taught in EP-A 83,975, and references cited therein, to prepare o-groups Q-1 to Q-30.

The heterocyclic amines of Formula VI in Equation 3 above can be prepared by methods known in the literature, or simple modifications thereof, by those skilled in the art. For instance, EP-A No. 84,224 (published July 27, 1983) and W. Braker et al., *J. Am. Chem. Soc.*, 69, 3072 (1947) describe methods for preparing aminopyrimidines and triazines substituted by acetal groups such as dialkoxymethyl or 1,3-dioxolan-2-yl, among other groups. Also, for example, South African patent application Nos. 825,045 and 825,671 describe methods for preparing aminopyrimidines and triazines substituted by halogenoalkyl or halogenalkylthio groups such as OCH₂CH₂F, OCH₂CF₃, SCF₂H or OCF₂H, among other groups. Also, for example, South African patent application No. 837,434 (published Oct. 5, 1983) describes methods for the synthesis of cyclopropylpyrimidines and triazines substituted by such groups as alkyl, haloalkyl, alkoxy, haloalkoxy, alkylamino, dialkylamino or alkoxyalkyl.

Also, the 5,6-dihydrofuro[2.3-d]pyrimidin-2-amines, the cyclopenta[d]pyrimidin-2-amines (VI, A is A-2) and the 6,7-dihydro-5H-pyrano[2.3-d]pyrimidin-2-amines (VI, A is A-3) can be prepared as described in EP-A No. 15,683. Also, the furo[2.3-d]pyrimidin-2-amines (VI, A is A-4) are described in EP-A No. 46,677.

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describe the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is further illustrated by the following specific examples. Unless otherwise indicated, temperatures are in degrees centigrade.

EXAMPLE 1

2-(Aminosulfonyl)benzeneacetic acid, hydrazide

To a suspension of 30 g of methyl 2-(aminosulfonyl)-benzeneacetate in 125 ml of absolute ethanol was added 7.8 g of hydrazine monohydrate. The suspension was heated at reflux for about 16 hours, then cooled in an ice-water bath. A viscous oil formed which solidified on continued stirring and cooling. The suspension was filtered and suction-dried to give 23 g of the subject compound; m.p. 116°–125° C. Anal. Calc. for: $C_8H_{11}N_3O_3S$; C,41.9; H,4.8; N,18.3. Found: C,41.5; H,4.9; N,18.0.

EXAMPLE 2

2-[(5-Mercapto-1,3,4-thiadiazol-2-yl)methyl]benzenesulfonamide

To a suspension of 22 g of the hydrazide prepared in Example 1 in 175 ml of absolute ethanol was added a solution of 5.4 g of potassium hydroxide in 40 ml of water. After stirring several minutes, 9.2 g of carbon disulfide was added dropwise. The suspension was refluxed 4 hours then concentrated in vacuo. After water (about 200 ml) was added to the residue and the suspension stirred several minutes, the suspension was filtered, and the filtrate was acidified with concentrated hydrochloric acid (red to litmus paper). The mixture was filtered and the solid isolated was suction-dried to give 5 g of the crude subject compound; m.p. 173°–197° C.

EXAMPLE 3

2-[[5-(Methylthio)-1,3,4-thiadiazol-2-yl]methyl]benzenesulfonamide

To a solution containing 1.0 g of potassium hydroxide in 50 ml of methanol was added 5 g of the crude oxadiazole prepared in Example 2. After stirring about five minutes, 3.5 g of methyl iodide was added. The solution was refluxed one hour, cooled to 30°, an extra 10 ml of methyl iodide was added, and the solution was refluxed an additional two hours, then concentrated in vacuo. After water (about 150 ml) was added to the residue, the suspension was extracted with methylene chloride. The methylene chloride solution was dried ($MgSO_4$), concentrated in vacuo, and the residue was recrystallized from acetonitrile to give 0.8 g of the subject compound; m.p. 175°–178° C. NMR($CDCl_3$, DMSO-$d_6$): δ 2.8(s, $SCH_3$); 4.9(s, $CH_2$); 7.3(s, $NH_2$); 7.4–8.3 (m, ar) ppm. Mass spectrum by direct probe using electron impact ionization showed highest significant m/e 301.

EXAMPLE 4

N-[(4,6-Dimethoxypyrimidin-2-yl)aminocarbonyl]-2-[[5-(methylthio)-1,3,4-thiadiazol-2-yl]methyl]benzenesulfonamide To a suspension containing 0.63 g of the sulfonamide prepared in Example 3 in 10 ml of p-dioxane was added 0.6 g phenyl(4,6-dimethoxypyrimidin-2-yl)carbamate followed by dropwise addition of 0.33 g of 1.8-diazabicyclo[5.4.0]undec-7-ene (DBU). The solution was stirred at room temperature for two hours then diluted with about 75 ml of water. After extracting the cloudy aqueous solution 1×30 ml of diethyl ether, the clear aqueous layer was acidified with concentrated hydrochloric acid (red to litmus paper), and the suspension was filtered. The residue was triturated with 5 ml of warm ethyl acetate to give 0.2 g of the subject compound; m.p. 171°–175° C. NMR ($CDCl_3$, DMSO-$d_6$): δ 2.7(s, $SCH_3$); 4.0(s, $OCH_3$); 4.95(s, $CH_2$); 5.9(s, pyrimidine H); 7.6–8.4(m, ar); 9.8(s, NH) ppm.

EXAMPLE 5

N-[(4-Methoxy-6-methyl-1,3,5-triazin-2-yl)aminocarbonyl]-2-[[5-(methylthio)-1,3,4-thiadiazol-2-yl]methyl]-benzenesulfonamide By the procedure of Example 4, 0.3 g of the sulfonamide prepared in Example 3 was reacted with 0.29 g of phenyl(4-methoxy-6-methyl-1,3,5-triazin-2-yl)carbamate and 0.15 g of "DBU" in 10 ml of p-dioxane. After stirring two hours at room temperature the solution was diluted with about 75 ml of water and acidified with concentrated hydrochloric acid (red to litmus paper). Following filtration, the residue was washed with water (2×20ml) then with ether (1×20ml) and suction-dried to give 0.15 g of the subject compound; m.p. 140°–146° C. NMR ($CDCl_3$): δ2.6(d,6H,$SCH_3$, $OCH_3$); 4.1 (S, 3H, $CH_3$); 4.9(S, 2H, $CH_2$); 7.4–7.7(m, 4H, Ar+NH); 8.3(d, 1H, Ar).

EXAMPLE 6

1-[[2-(Phenylmethylthio)phenyl]methyl]-1H-1,2,4-triazole

To a suspension of 9.9 g of potassium t-butoxide in 100 ml of DMF under a $N_2$ atmosphere was added portion wise 6 g of 1,2,4-triazole. After stirring at ambient temperature for one hour, a solution of 20 g of 2-benzylmercaptobenzyl chloride in 15 ml of DMF was added dropwise and the suspension was heated at 70° C. for 4 hours, then stirred at 25° C. 16 hours. After pouring the suspension into excess ice-water the residue was extracted with methylene chloride, dried (MgSO$_4$), and the solvent was evaporated in vacuo to an oil residue which solidified to 14.5 g of the subject compound when triturated with 1-chlorobutane; m.p. 65°–68° C.

EXAMPLE 7

2-[(1H-1,2,4-triazol-1yl)methyl]benzenesulfonamide (a) To a solution of 10 g of the product of Example 6 and 1.9 g of water in 100 ml of propionic acid was added dropwise 9.1 ml of chlorine; the temperature of the resulting reaction was maintained at −5° to 0° C. with external cooling. After stirring at 0° for one hour the suspension was cooled to −20° C. and filtered. The residue was washed with 40 ml of hexane and suction-dried to yield 4 g of 2-[(1H-1,2,4-triazol-1-yl)methyl]-benzenesulfonyl chloride as a crude solid; m.p. 180°–195° C.

(b) To a suspension of 3 g of the above sulfonyl chloride in 125 ml of tetrahydrofuran was added dropwise about 25 ml of concentrated aqueous NH$_4$OH at 10° to 19° C. with external cooling. After stirring at 25° C. one hour, the organic solvent (tetrahydrofuran) was evaporated in vacuo and the residue was diluted with excess ice-water, then filtered. The isolated solid was dried in 100 ml of tetrahydrofuran over MgSO$_4$ and, after evaporation of the solvent, the oil residue was triturated with 1-chlorobutane to yield 1.7 g of the subject compound; m.p. 128°–131° C. NMR(CDCl$_3$):ppm 5.9(d, 4H, CH$_2$+SO$_2$NH$_2$) 7.3–7.6(m, 4H, Ar)7.9 and 8.3(2S, 2H, tri 2H) 8.1(m, 1H, Ar).

EXAMPLE 8

N-[(4,6-Dimethoxypyrimidin-2-yl)aminocarbonyl]-2-[(1H-1,2,4-triazol-2-yl)methyl]benzenesulfonamide By the procedure of Example 4, 0.4 g of the product of Example 7 was reacted with 0.52 g of phenyl(4,6-dimethoxypyrimidin-2-yl)carbamate and 0.26 g of "DBU" in 10 ml of p-dioxane. After stirring at 25° C. for two hours, the resulting suspension was diluted with about 50 ml of water, and filtered; the resulting filtrate was acidified with concentrated hydrochloric acid to pH 4, then filtered. The residue was washed 2×10 ml water, suction-dried 16 hours, then triturated with about 10 ml of warm ethyl acetate to yield 0.5 g of the subject compound; m.p. 219°–220° C. IR(nujol): 1690 cm$^{-1}$ (c=o); NMR(CDCl$_3$): ppm 3.9(S, 6H, OCH$_3$); 5.8(S, 1H, py H); 6.0(S, 2H, CH$_2$); 7.9 and 8.2(2S, 2H, tri 2H); 7.1–7.6(m, 4H, Ar+NH); 8.15(m, 1H, Ar).

Using the techniques described in Equations 1–11 and Examples 4, 5 and 8, or simple modifications thereof, obvious to one skilled in the art, the following compounds in Tables I–V can be made.

TABLE I

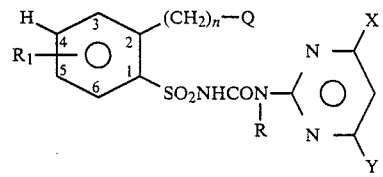

| Q | R | R$_1$ | n | X | Y | m.p. °C. |
|---|---|---|---|---|---|---|
| Q-1 (R$_5$ = H, R$_6$ = CH$_3$) | H | H | 1 | CH$_3$ | CH$_3$ | |
| Q-1 (R$_5$ = CH$_3$, R$_6$ = H) | H | H | 1 | OCH$_3$ | OCH$_3$ | |
| Q-1 (R$_5$ = H, R$_6$ = CH$_3$) | H | H | 1 | CH$_3$ | OCH$_3$ | |
| Q-1 (R$_5$ = CH$_3$, R$_6$ = H) | H | H | 1 | Cl | OCH$_3$ | |
| Q-1 (R$_5$ = H, R$_6$ = CH$_3$) | H | H | 2 | OCH$_3$ | OCH$_3$ | |
| Q-1 (R$_5$ = CH$_3$, R$_6$ = H) | CH$_3$ | H | 1 | OCH$_3$ | OCH$_3$ | |
| Q-1 (R$_5$ = CH$_3$, R$_6$ = CH$_3$) | H | H | 1 | OCH$_3$ | OCH$_3$ | |
| Q-1 (R$_5$ = CH$_3$, R$_6$ = CH$_3$) | H | H | 1 | OCH$_3$ | OCH$_3$ | |
| Q-2 (R$_5$ = H, R$_6$ = CH$_3$) | H | H | 1 | CH$_3$ | CH$_3$ | |
| Q-2 (R$_5$ = CH$_3$, R$_6$ = H) | H | H | 1 | OCH$_3$ | OCH$_3$ | |
| Q-2 (R$_5$ = H, R$_6$ = CH$_3$) | H | H | 1 | CH$_3$ | OCH$_3$ | |
| Q-2 (R$_5$ = CH$_3$, R$_6$ = H) | H | H | 1 | Cl | OCH$_3$ | |
| Q-2 (R$_5$ = H, R$_6$ = CH$_3$) | H | H | 2 | OCH$_3$ | OCH$_3$ | |
| Q-2 (R$_5$ = CH$_3$, R$_6$ = H) | H | H | 2 | OCH$_3$ | CH$_3$ | |
| Q-2 (R$_5$ = H, R$_6$ = CH$_3$) | CH$_3$ | H | 1 | OCH$_3$ | OCH$_3$ | |
| Q-2 (R$_5$ = CH$_3$, R$_6$ = CH$_3$) | H | H | 1 | OCH$_3$ | OCH$_3$ | |
| Q-2 (R$_5$ = CH$_3$, R$_6$ = CH$_3$) | H | H | 1 | OCH$_3$ | OCH$_3$ | |
| Q-3 (R$_5$ = CH$_3$) | H | H | 1 | CH$_3$ | CH$_3$ | |
| Q-3 (R$_5$ = CH$_3$) | H | H | 1 | OCH$_3$ | OCH$_3$ | |
| Q-3 (R$_5$ = CH$_3$) | H | H | 1 | CH$_3$ | OCH$_3$ | |
| Q-3 (R$_5$ = CH$_3$) | H | H | 1 | Cl | OCH$_3$ | |
| Q-3 (R$_5$ = CH$_3$) | H | H | 2 | OCH$_3$ | OCH$_3$ | |
| Q-3 (R$_5$ = CH$_3$) | CH$_3$ | H | 1 | OCH$_3$ | OCH$_3$ | |
| Q-4 (R$_5$ = H, R$_6$ = CH$_3$) | H | H | 1 | OCH$_3$ | OCH$_3$ | |
| Q-4 (R$_5$ = CH$_3$, R$_6$ = H) | H | H | 2 | OCH$_3$ | OCH$_3$ | |
| Q-5 (R$_5$ = H, R$_6$ = CH$_3$) | H | H | 1 | OCH$_3$ | OCH$_3$ | |
| Q-5 (R$_5$ = CH$_3$, R$_6$ = H) | H | H | 2 | OCH$_3$ | OCH$_3$ | |
| Q-6 (R$_5$ = H, R$_6$ = CH$_3$) | H | H | 1 | OCH$_3$ | CH$_3$ | |
| Q-7 (R$_5$ = H, R$_6$ = H) | H | H | 1 | OCH$_3$ | CH$_3$ | |
| Q-6 (R$_5$ = CH$_3$, R$_6$ = H) | H | H | 2 | OCH$_3$ | OCH$_3$ | |
| Q-7 (R$_5$ = H, R$_6$ = H) | H | H | 2 | OCH$_3$ | OCH$_3$ | |
| Q-8 (R$_5$ = H, R$_6$ = CH$_3$) | H | H | 1 | OCH$_3$ | CH$_3$ | |
| Q-8 (R$_5$ = CH$_3$, R$_6$ = H) | H | H | 2 | OCH$_3$ | CH$_3$ | |
| Q-9 (R$_5$, R$_6$, R$_7$ = H) | H | H | 1 | CH$_3$ | CH$_3$ | |

TABLE I-continued

| Q | R | R₁ | n | X | Y | m.p. °C. |
|---|---|---|---|---|---|---|
| Q-9 (R₅, R₆, R₇ = H) | H | H | 1 | OCH₃ | OCH₃ | |
| Q-9 (R₅, R₆, R₇ = H) | H | H | 1 | OCH₃ | CH₃ | |
| Q-9 (R₅, R₆, R₇ = H) | H | H | 1 | Cl | OCH₃ | |
| Q-9 (R₅, R₆, R₇ = H) | H | H | 2 | OCH₃ | OCH₃ | |
| Q-9 (R₅, R₇ = CH₃; R₆ = H) | H | H | 1 | OCH₃ | OCH₃ | |
| Q-13 (R₈ = SCH₃) | H | H | 1 | CH₃ | CH₃ | 205–206 |
| Q-13 (R₈ = SCH₃) | H | H | 1 | OCH₃ | OCH₃ | 171–174 |
| Q-13 (R₈ = SCH₃) | H | H | 1 | CH₃ | OCH₃ | 170–172 |
| Q-13 (R₈ = SCH₃) | H | H | 1 | Cl | OCH₃ | 167–171 |
| Q-10 (R₈ = SCH₃) | H | H | 2 | CH₃ | CH₃ | |
| Q-10 (R₈ = SCH₃) | H | H | 2 | OCH₃ | OCH₃ | |
| Q-10 (R₈ = SCH₃) | H | H | 2 | CH₃ | OCH₃ | |
| Q-10 (R₈ = SCH₃) | H | H | 2 | Cl | OCH₃ | |
| Q-10 (R₈ = SCH₃) | CH₃ | H | 1 | OCH₃ | OCH₃ | |
| Q-13 (R₈ = SC₂H₅) | H | H | 1 | CH₃ | CH₃ | |
| Q-13 (R₈ = SC₂H₅) | H | H | 1 | OCH₃ | OCH₃ | |
| Q-13 (R₈ = SC₂H₅) | H | H | 1 | CH₃ | OCH₃ | |
| Q-13 (R₈ = SC₂H₅) | H | H | 1 | Cl | OCH₃ | |
| Q-13 (R₈ = SC₂H₅) | H | H | 2 | OCH₃ | OCH₃ | |
| Q-10 (R₈ = SCH₃) | H | H | 1 | CH₃ | CH₃ | |
| Q-10 (R₈ = SCH₃) | H | H | 1 | OCH₃ | OCH₃ | |
| Q-10 (R₈ = SCH₃) | H | H | 1 | CH₃ | OCH₃ | |
| Q-10 (R₈ = SCH₃) | H | H | 1 | Cl | OCH₃ | |
| Q-10 (R₈ = SCH₃) | H | H | 2 | OCH₃ | OCH₃ | |
| Q-10 (R₈ = SC₂H₅) | H | H | 1 | OCH₃ | OCH₃ | |
| Q-10 (R₈ = OCH₃) | H | H | 1 | CH₃ | CH₃ | |
| Q-10 (R₈ = OCH₃) | H | H | 1 | OCH₃ | OCH₃ | |
| Q-10 (R₈ = OCH₃) | H | H | 1 | CH₃ | OCH₃ | |
| Q-10 (R₈ = OCH₃) | H | H | 1 | Cl | OCH₃ | |
| Q-10 (R₈ = OCH₃) | H | H | 2 | OCH₃ | OCH₃ | |
| Q-10 (R₈ = OC₂H₅) | H | H | 1 | OCH₃ | OCH₃ | |
| Q-10 (R₈ = SCH₂CN) | H | H | 1 | CH₃ | CH₃ | |
| Q-10 (R₈ = SCH₂CN) | H | H | 1 | OCH₃ | OCH₃ | |
| Q-10 (R₈ = SCH₂CN) | H | H | 1 | CH₃ | OCH₃ | |
| Q-10 (R₈ = SCH₂CN) | H | H | 1 | Cl | OCH₃ | |
| Q-10 (R₈ = SCH₂CN) | H | H | 2 | OCH₃ | OCH₃ | |
| Q-13 (R₈ = SCF₂H) | H | H | 1 | CH₃ | CH₃ | |
| Q-13 (R₈ = SCF₂H) | H | H | 1 | OCH₃ | OCH₃ | |
| Q-13 (R₈ = SCF₂H) | H | H | 1 | CH₃ | OCH₃ | |
| Q-13 (R₈ = SCF₂H) | H | H | 1 | Cl | OCH₃ | |
| Q-13 (R₈ = SCF₂H) | H | H | 2 | OCH₃ | OCH₃ | |
| Q-14 (R₉ = Cl) | H | H | 1 | OCH₃ | OCH₃ | |
| Q-14 (R₉ = Cl) | H | H | 1 | CH₃ | OCH₃ | |
| Q-14 (R₉ = Cl) | H | H | 2 | OCH₃ | OCH₃ | |
| Q-14 (R₉ = Cl) | CH₃ | H | 1 | OCH₃ | OCH₃ | |
| Q-17 | H | H | 1 | OCH₃ | OCH₃ | |
| Q-17 | H | H | 1 | CH₃ | OCH₃ | |
| Q-17 | H | H | 1 | Cl | OCH₃ | |
| Q-18 (R₅ = CH₃) | H | H | 1 | OCH₃ | OCH₃ | |
| Q-19 (R₅ = CH₃) | H | H | 1 | OCH₃ | OCH₃ | |
| Q-20 (R₅ = H, R₆ = H) | H | H | 1 | OCH₃ | OCH₃ | 219–220 |
| Q-20 (R₅ = H, R₆ = H) | H | H | 1 | CH₃ | OCH₃ | 215–218 |
| Q-20 (R₅ = H, R₆ = H) | H | H | 1 | CH₃ | CH₃ | 206–208 |
| Q-20 (R₅ = H, R₆ = H) | H | H | 1 | Cl | OCH₃ | 224–226 |
| Q-20 (R₅ = H, R₆ = H) | H | H | 2 | OCH₃ | OCH₃ | |
| Q-20 (R₅ = CH₃, R₆ = H) | H | H | 1 | OCH₃ | OCH₃ | |
| Q-20 (R₅ = H, R₆ = CH₃) | H | H | 1 | OCH₃ | OCH₃ | |
| Q-21 (R₅ = CH₃) | H | H | 1 | OCH₃ | OCH₃ | |
| Q-22 (R₅ = H, R₆ = H) | H | H | 1 | OCH₃ | OCH₃ | |
| Q-23 (R₅ = H, R₆ = CH₃) | H | H | 1 | OCH₃ | OCH₃ | |
| Q-23 (R₅ = CH₃, R₆ = H) | H | H | 1 | CH₃ | OCH₃ | |
| Q-23 (R₅ = H, R₆ = CH₃) | H | H | 1 | CH₃ | CH₃ | |
| Q-23 (R₅ = CH₃, R₆ = H) | H | H | 1 | Cl | OCH₃ | |
| Q-23 (R₅ = H, R₆ = CH₃) | H | H | 2 | OCH₃ | OCH₃ | |
| Q-24 (R₅ = CH₃, R₆ = H) | H | H | 1 | OCH₃ | OCH₃ | |
| Q-24 (R₅ = H, R₆ = CH₃) | H | H | 1 | CH₃ | OCH₃ | |
| Q-24 (R₅ = CH₃, R₆ = H) | H | H | 1 | CH₃ | CH₃ | |
| Q-24 (R₅ = H, R₆ = CH₃) | H | H | 1 | Cl | OCH₃ | |
| Q-25 (R₅ = CH₃, R₆ = H) | H | H | 1 | OCH₃ | OCH₃ | |
| Q-26 (R₅ = CH₃, R₆ = CH₃) | H | H | 1 | OCH₃ | OCH₃ | |
| Q-27 (R₅ = H, R₆ = CH₃) | H | H | 1 | OCH₃ | OCH₃ | |

TABLE I-continued

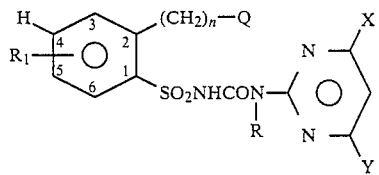

| Q | R | R₁ | n | X | Y | m.p. °C. |
|---|---|---|---|---|---|---|
| Q-28 ($R_5$ = H, $R_6$ = $CH_3$) | H | H | 1 | $OCH_3$ | $OCH_3$ | |
| Q-29 ($R_5$ = H, $R_6$ = $CH_3$) | H | H | 1 | $OCH_3$ | $CH_3$ | |
| Q-30 ($R_5$—$R_7$ = H) | H | H | 1 | $OCH_3$ | $OCH_3$ | |
| Q-30 ($R_5$, $R_6$ = H; $R_7$ = $CH_3$) | H | H | 1 | $OCH_3$ | $OCH_3$ | |
| Q-31 ($R_5$—$R_7$ = $CH_3$) | H | H | 1 | $OCH_3$ | $OCH_3$ | |
| Q-31 ($R_5$—$R_7$ = $CH_3$) | H | H | 2 | $OCH_3$ | $OCH_3$ | |
| Q-31 ($R_5$, $R_6$ = H; $R_7$ = $CH_3$) | H | H | 1 | $OCH_3$ | $OCH_3$ | |
| Q-32 ($R_5$—$R_7$ = H) | H | H | 1 | $OCH_3$ | $CH_3$ | |
| Q-33 ($R_5$—$R_7$ = $CH_3$) | H | H | 1 | $OCH_3$ | $OCH_3$ | |
| Q-34 ($R_5$—$R_7$ = H) | H | H | 1 | $OCH_3$ | $OCH_3$ | |
| Q-35 ($R_5$—$R_7$ = H) | H | H | 1 | $CH_3$ | $OCH_3$ | |
| Q-35 ($R_5$, $R_6$ = H; $R_7$ = $CH_3$) | H | H | 1 | $OCH_3$ | $OCH_3$ | |
| Q-36 ($R_5$—$R_7$ = H) | H | H | 1 | $OCH_3$ | $OCH_3$ | |
| Q-37 ($R_5$—$R_7$ = H) | H | H | 1 | $OCH_3$ | $OCH_3$ | |
| Q-37 ($R_5$—$R_7$ = H) | H | H | 2 | $OCH_3$ | $OCH_3$ | |
| Q-38 ($R_5$—$R_7$ = H) | H | H | 1 | $OCH_3$ | $OCH_3$ | |
| Q-40 ($R_5$ = H) | H | H | 1 | $OCH_3$ | $CH_3$ | |
| Q-41 ($R_5$ = H) | H | H | 1 | $OCH_3$ | $CH_3$ | |
| Q-43 ($R_5$ = H) | H | H | 1 | $CH_3$ | $CH_3$ | |
| Q-44 ($R_5$ = H) | H | H | 1 | $OCH_3$ | $OCH_3$ | |
| Q-45 ($R_5$, $R_6$ = $CH_3$) | H | H | 1 | $OCH_3$ | $OCH_3$ | |
| Q-46 ($R_5$, $R_6$ = $CH_3$) | H | H | 1 | $OCH_3$ | $OCH_3$ | |
| Q-47 ($R_5$, $R_6$ = $CH_3$) | H | H | 1 | $OCH_3$ | $OCH_3$ | |
| Q-48 ($R_5$, $R_{11}$, $R_{12}$ = $CH_3$) | H | H | 1 | $CH_3$ | $OCH_3$ | |
| Q-48 ($R_{11}$, $R_{12}$ = $OCH_3$; $R_5$ = H) | H | H | 1 | $OCH_3$ | $OCH_3$ | |
| Q-48 ($R_5$ = H; $R_{11}$, $R_{12}$ = $CH_3$) | H | H | 1 | $OCH_3$ | $OCH_3$ | |
| Q-48 ($R_5$, $R_{11}$, $R_{12}$ = $CH_3$) | H | H | 2 | $OCH_3$ | $OCH_3$ | |
| Q-49 ($R_{11}$, $R_{12}$ = $CH_3$) | H | H | 1 | $OCH_3$ | $OCH_3$ | |
| Q-50 ($R_{11}$, $R_{12}$ = $CH_3$) | H | H | 1 | $OCH_3$ | $OCH_3$ | |
| Q-51 ($R_5$, $R_6$ = $CH_3$) | H | H | 1 | $CH_3$ | $OCH_3$ | |
| Q-52 ($R_5$, $R_6$ = $CH_3$) | H | H | 1 | $OCH_3$ | $OCH_3$ | |
| Q-53 ($R_{13}$, $R_{14}$ = $CH_3$) | H | H | 1 | $OCH_3$ | $OCH_3$ | |
| Q-53 ($R_{13}$, $R_{14}$ = $OCH_3$) | H | H | 1 | $OCH_3$ | $OCH_3$ | |
| Q-54 ($R_{13}$, $R_{14}$ = $CH_3$) | H | H | 1 | $OCH_3$ | $CH_3$ | |
| Q-54 ($R_{13}$, $R_{14}$ = $OCH_3$) | H | H | 1 | $OCH_3$ | $OCH_3$ | |
| Q-13 ($R_8$ = $SCH_3$) | H | 6-Cl | 1 | $OCH_3$ | $OCH_3$ | |
| Q-13 ($R_8$ = $SCH_3$) | H | 6-$CH_3$ | 1 | $OCH_3$ | $OCH_3$ | |
| Q-13 ($R_8$ = $SCH_3$) | H | 5-$CF_3$ | 1 | $OCH_3$ | $OCH_3$ | |
| Q-13 ($R_8$ = $SCH_3$) | H | 5-$OCH_3$ | 1 | $OCH_3$ | $OCH_3$ | |
| Q-13 ($R_8$ = $SCH_3$) | H | 5-$OCF_2H$ | 1 | $OCH_3$ | $OCH_3$ | |
| Q-20 ($R_5$, $R_6$ = H) | H | 6-$SCF_2H$ | 2 | $OCH_3$ | $OCH_3$ | |
| Q-10 ($R_8$ = $SCH_3$) | H | H | 1 | $OC_2H_5$ | $CH_3$ | |
| Q-10 ($R_8$ = $OCH_3$) | H | H | 1 | F | $OCH_3$ | |
| Q-10 ($R_8$ = $OCH_2CH_3$) | H | H | 1 | Br | $OCH_3$ | |
| Q-24 ($R_5$, $R_6$ = $CH_3$) | H | H | 1 | $CH_2F$ | $CH_3$ | |
| Q-14 ($R_9$ = Cl) | H | H | 1 | $OCH_2CH_2F$ | $CH_3$ | |
| Q-1 ($R_5$, $R_6$ = $CH_3$) | H | H | 1 | $OCH_2CHF_2$ | $CH_3$ | |
| Q-20 ($R_5$, $R_6$ = H) | H | H | 1 | $OCH_2CF_3$ | $OCH_3$ | |
| Q-10 ($R_8$ = $SCH_3$) | H | H | 1 | F | $OCH_3$ | |
| Q-10 ($R_8$ = $OCH_3$) | H | H | 1 | I | $OCH_3$ | |
| Q-10 ($R_8$ = $SCH_2CH_3$) | H | H | 1 | $OCF_2H$ | $OCH_3$ | |
| Q-10 ($R_8$ = $OCH_2CH_3$) | H | H | 1 | $CH_2F$ | $OCH_3$ | |
| Q-10 ($R_8$ = $SCF_2H$) | H | H | 1 | $OCH_2CH_2F$ | $CH_3$ | |
| Q-10 ($R_8$ = $SCH_3$) | H | H | 1 | $OCH_2CHF_2$ | $CH_3$ | |
| Q-10 ($R_8$ = $SCH_3$) | H | H | 1 | $OCH_2CF_3$ | $CH_3$ | |
| Q-10 ($R_8$ = $SCH_3$) | H | H | 1 | $OCH_2CF_3$ | $OCH_3$ | |
| Q-10 ($R_8$ = $SCH_3$) | H | H | 1 | $CF_3$ | $OCH_3$ | |
| Q-10 ($R_8$ = $SCH_3$) | H | H | 1 | $OCH_3$ | H | |
| Q-1 ($R_5$, $R_6$ = $CH_3$) | H | H | 2 | Cl | $OC_2H_5$ | |
| Q-2 ($R_5$, $R_6$ = $CH_3$) | H | H | 1 | $OCH_3$ | $CH_2OCH_3$ | |
| Q-3 ($R_5$ = $CH_3$) | H | H | 1 | Cl | $NHCH_3$ | |
| Q-10 ($R_8$ = $OCH_3$) | H | H | 1 | $OC_2H_5$ | $N(OCH_3)CH_3$ | |
| Q-10 ($R_8$ = $OCH_3$) | H | H | 1 | $CH_3$ | $N(CH_3)_2$ | |
| Q-6 ($R_5$, $R_6$ = $CH_3$) | H | H | 1 | $OCH_3$ | $C_2H_5$ | |
| Q-10 ($R_8$ = $SCH_3$) | H | H | 2 | $OCH_3$ | $OCH_2CH=CH_2$ | |
| Q-10 ($R_8$ = $OCH_3$) | H | H | 1 | $CH_3$ | $OCH_2C\equiv CH$ | |
| Q-14 ($R_9$ = Cl) | H | H | 1 | $CH_3$ | $OCH_2CH_2OCH_3$ | |
| Q-10 ($R_8$ = $SCH_3$) | H | H | 1 | $CH_3$ | $CH_2SCH_3$ | |
| Q-10 ($R_8$ = $OCH_3$) | H | H | 1 | $CH_3$ | CHO | |

TABLE I-continued

| Q | R | $R_1$ | n | X | Y | m.p. °C. |
|---|---|---|---|---|---|---|
| Q-24 ($R_5, R_6$ = CH$_3$) | H | H | 1 | CH$_3$ | $\overset{O}{\underset{\|}{C}}CH_3$ | |
| Q-10 ($R_8$ = SCH$_3$) | H | H | 1 | OCH$_3$ | CH(OCH$_3$)$_2$ | |
| Q-20 ($R_5, R_6$ = H) | H | H | 2 | OCH$_3$ | CH(OC$_2$H$_5$)$_2$ | |
| Q-31 ($R_5, R_6, R_7$ = CH$_3$) | H | H | 1 | OCH$_3$ | CH(SCH$_3$)$_2$ | |
| Q-35 ($R_5, R_6, R_7$ = H) | H | H | 1 | OCH$_3$ | C(CH$_3$)(OCH$_3$)$_2$ | |
| Q-10 ($R_8$ = SCH$_3$) | H | H | 1 | OCH$_3$ | 1,3-dioxolan-2-yl | |
| Q-1 ($R_5, R_6$ = CH$_3$) | H | H | 1 | OCH$_3$ | 1,3-oxathiolan-2-yl | |
| Q-2 ($R_5, R_6$ = CH$_3$) | H | H | 1 | OCH$_3$ | 2-methyl-1,3-dioxolan-2-yl | |
| Q-10 ($R_8$ = SCH$_3$) | H | H | 1 | OCH$_3$ | 4-methyl-1,3-dioxolan-2-yl | |
| Q-20 ($R_5, R_6$ = H) | H | H | 2 | OCH$_3$ | 4-methyl-1,3-oxathiolan-2-yl | |
| Q-3 ($R_5$ = CH$_3$) | H | H | 1 | OCH$_3$ | 4-methyl-1,3-dithiolan-2-yl | |
| Q-24 ($R_5, R_6$ = CH$_3$) | H | H | 1 | OCH$_3$ | 2,4-dimethyl-1,3-dioxolan-2-yl | |
| Q-10 ($R_8$ = SCH$_3$) | H | H | 1 | CH$_3$ | SCF$_2$H | |
| Q-10 ($R_8$ = SCH$_3$) | H | H | 1 | Cl | OCF$_2$H | |
| Q-10 ($R_8$ = SCH$_3$) | H | H | 1 | OCH$_3$ | cyclopropyl | |
| Q-51 ($R_5, R_6$ = CH$_3$) | H | H | 2 | OCH$_3$ | OCH$_3$ | |
| Q-48 ($R_5, R_{11}, R_{12}$ = CH$_3$) | H | H | 2 | OCH$_3$ | OCH$_3$ | |
| Q-45 ($R_5, R_6$ = CH$_3$) | H | H | 2 | OCH$_3$ | OCH$_3$ | |
| Q-46 ($R_5, R_6$ = CH$_3$) | H | H | 2 | OCH$_3$ | OCH$_3$ | |
| Q-47 ($R_5, R_6$ = CH$_3$) | H | H | 2 | OCH$_3$ | OCH$_3$ | |
| Q-13 ($R_8$ = SCH$_2$CH=CH$_2$) | H | H | 1 | CH$_3$ | CH$_3$ | |
| Q-13 ($R_8$ = SCH$_2$CH=CH$_2$) | H | H | 1 | OCH$_3$ | CH$_3$ | |
| Q-13 ($R_8$ = SCH$_2$CH=CH$_2$) | H | H | 1 | OCH$_3$ | OCH$_3$ | |
| Q-13 ($R_8$ = SCH$_2$CH=CH$_2$) | H | H | 1 | Cl | OCH$_3$ | |
| Q-13 ($R_8$ = SCH$_2$CN) | H | H | 1 | CH$_3$ | OCH$_3$ | |
| Q-13 ($R_8$ = SCH$_2$CN) | H | H | 1 | CH$_3$ | CH$_3$ | |
| Q-13 ($R_8$ = SCH$_2$CN) | H | H | 1 | OCH$_3$ | OCH$_3$ | |

TABLE I-continued

| Q | R | R₁ | n | X | Y | m.p. °C. |
|---|---|----|---|---|---|----------|
| Q-13 (R₈ = SCH₂CN) | H | H | 1 | Cl | OCH₃ | |
| Q-10 (R₈ = OCH₃) | H | H | 1 | OCH₃ | CH₂OCH₃ | |
| Q-10 (R₈ = OCH₃) | H | H | 1 | OCF₂H | CH₃ | |
| Q-10 (R₈ = SCH₃) | H | H | 1 | Br | OCH₃ | |
| Q-10 (R₈ = OCH₃) | H | H | 1 | OC₂H₅ | CH₃ | |
| Q-10 (R₈ = SCH₂CH₃) | H | H | 1 | OCF₂H | OCH₃ | |
| Q-10 (R₈ = OCH₂CH₃) | H | H | 1 | OCF₂H | CH₃ | |
| Q-10 (R₈ = SCF₂H) | H | H | 1 | OCH₃ | CH(OCH₃)₂ | |
| Q-10 (R₈ = SCF₂H) | H | H | 1 | OCH₃ | CH₂OCH₃ | |
| Q-9 (R₅, R₇ = CH₃, R₆ = H) | H | H | 1 | OCH₃ | OCH₃ | |
| Q-9 (R₅, R₇ = CH₃, R₆ = H) | H | H | 1 | CH₃ | OCH₃ | |
| Q-9 (R₅, R₇ = CH₃, R₆ = H) | H | H | 1 | Cl | OCH₃ | |
| Q-9 (R₅, R₇ = CH₃, R₆ = H) | H | H | 1 | CH₃ | CH₃ | |
| Q-13 (R₈ = SH) | H | H | 1 | CH₃ | OCH₃ | |
| Q-13 (R₈ = SH) | H | H | 1 | CH₃ | CH₃ | |
| Q-13 (R₈ = SH) | H | H | 1 | Cl | OCH₃ | |
| Q-20 (R₅, R₆ = H) | H | H | 2 | CH₃ | OCH₃ | |
| Q-20 (R₅, R₆ = H) | H | H | 2 | CH₃ | CH₃ | |
| Q-20 (R₅, R₆ = H) | H | H | 2 | Cl | OCH₃ | |

TABLE II

| Q | R₁ | R | n | X | Y | m.p. °C. |
|---|----|---|---|---|---|----------|
| Q-1 (R₅,R₆ = CH₃) | H | H | 1 | OCH₃ | CH₃ | |
| Q-1 (R₅,R₆ = CH₃) | H | H | 1 | OCH₃ | OCH₃ | |
| Q-1 (R₅,R₆ = CH₃) | H | H | 2 | OCH₃ | CH₃ | |
| Q-1 (R₅,R₆ = CH₃) | H | CH₃ | 1 | OCH₃ | CH₃ | |
| Q-1 (R₅ = CH₃,R₆ = H) | H | H | 1 | OCH₃ | CH₃ | |
| Q-1 (R₅ = H,R₆ = CH₃) | H | H | 1 | OCH₃ | CH₃ | |
| Q-2 (R₅ = H,R₆ = CH₃) | H | H | 1 | OCH₃ | CH₃ | |
| Q-2 (R₅ = CH₃,R₆ = H) | H | H | 1 | OCH₃ | OCH₃ | |
| Q-2 (R₅ = H,R₆ = CH₃) | H | H | 2 | OCH₃ | CH₃ | |
| Q-2 (R₅ = CH₃,R₆ = H) | H | CH₃ | 1 | CH₃ | OCH₃ | |
| Q-2 (R₅ = CH₃,R₆ = CH₃) | H | H | 1 | OCH₃ | CH₃ | |
| Q-2 (R₅ = CH₃,R₆ = CH₃) | H | H | 1 | OCH₃ | CH₃ | |
| Q-3 (R₅ = CH₃) | H | H | 1 | OCH₃ | CH₃ | |
| Q-3 (R₅ = CH₃) | H | H | 1 | CH₃ | OCH₃ | |
| Q-4 (R₅ = H,R₆ = CH₃) | H | H | 1 | CH₃ | OCH₃ | |
| Q-4 (R₅ = CH₃,R₆ = H) | H | H | 2 | OCH₃ | OCH₃ | |
| Q-5 (R₅ = H,R₆ = CH₃) | H | H | 1 | OCH₃ | CH₃ | |
| Q-6 (R₅ = CH₃,R₆ = H) | H | H | 1 | OCH₃ | CH₃ | |
| Q-7 (R₅ = H,R₆ = H) | H | H | 1 | OCH₃ | CH₃ | |
| Q-8 (R₅ = H,R₆ = CH₃) | H | H | 1 | OCH₃ | OCH₃ | |
| Q-9 (R₅,R₆,R₇ = H) | H | H | 1 | OCH₃ | CH₃ | |
| Q-9 (R₅,R₆,R₇ = H) | H | H | 1 | OCH₃ | OCH₃ | |
| Q-9 (R₅,R₆,R₇ = H) | H | H | 2 | OCH₃ | CH₃ | |
| Q-9 (R₅,R₇ = CH₃; R₆ = H) | H | H | 1 | OCH₃ | CH₃ | |
| Q-13 (R₈ = SCH₃) | H | H | 1 | OCH₃ | CH₃ | 140–146 |
| Q-13 (R₈ = SCH₃) | H | H | 1 | OCH₃ | OCH₃ | 155–159 |
| Q-10 (R₈ = SCH₃) | H | H | 2 | OCH₃ | CH₃ | |
| Q-10 (R₈ = SCH₃) | H | CH₃ | 1 | OCH₃ | CH₃ | |
| Q-13 (R₈ = SC₂H₅) | H | H | 1 | OCH₃ | CH₃ | |
| Q-13 (R₈ = SC₂H₅) | H | H | 1 | OCH₃ | OCH₃ | |
| Q-10 (R₈ = SC₂H₅) | H | H | 2 | OCH₃ | CH₃ | |
| Q-10 (R₈ = OCH₃) | H | H | 1 | OCH₃ | OCH₃ | |
| Q-10 (R₈ = OCH₃) | H | H | 1 | CH₃ | CH₃ | |
| Q-10 (R₈ = OCH₃) | H | H | 2 | OCH₃ | CH₃ | |
| Q-10 (R₈ = OCH₃) | H | CH₃ | 1 | OCH₃ | CH₃ | |
| Q-10 (R₈ = C₂H₅) | H | H | 1 | OCH₃ | CH₃ | |
| Q-10 (R₈ = OC₂H₅) | H | H | 1 | CH₃ | OCH₃ | |

TABLE II-continued

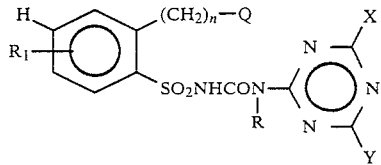

| Q | | R₁ | R | n | X | Y | m.p. °C. |
|---|---|----|---|---|---|---|----------|
| Q-10 | (R₈ = OC₂H₅) | H | H | 1 | OCH₃ | OCH₃ | |
| Q-10 | (R₈ = OC₂H₅) | H | H | 2 | OCH₃ | CH₃ | |
| Q-10 | (R₈ = OC₂H₅) | H | CH₃ | 1 | OCH₃ | CH₃ | |
| Q-10 | (R₈ = SH) | H | H | 1 | OCH₃ | CH₃ | |
| Q-10 | (R₈ = SH) | H | H | 1 | OCH₃ | OCH₃ | |
| Q-13 | (R₈ = SCF₂H) | H | H | 1 | OCH₃ | CH₃ | |
| Q-13 | (R₈ = SCF₂H) | H | H | 1 | OCH₃ | OCH₃ | |
| Q-13 | (R₈ = SCF₂H) | H | H | 2 | OCH₃ | CH₃ | |
| Q-13 | (R₈ = SCF₂H) | H | CH₃ | 1 | CH₃ | OCH₃ | |
| Q-14 | (R₉ = Cl) | H | H | 1 | OCH₃ | CH₃ | |
| Q-14 | (R₉ = Cl) | H | H | 1 | OCH₃ | OCH₃ | |
| Q-14 | (R₉ = Cl) | H | H | 2 | OCH₃ | CH₃ | |
| Q-14 | (R₉ = Cl) | H | CH₃ | 1 | OCH₃ | CH₃ | |
| Q-17 | | H | H | 1 | OCH₃ | CH₃ | |
| Q-17 | | H | H | 1 | OCH₃ | OCH₃ | |
| Q-18 | (R₅ = CH₃) | H | H | 1 | CH₃ | OCH₃ | |
| Q-19 | (R₅ = CH₃) | H | H | 1 | CH₃ | OCH₃ | |
| Q-20 | (R₅,R₆ = H) | H | H | 1 | OCH₃ | CH₃ | 179–182 |
| Q-20 | (R₅,R₆ = H) | H | H | 1 | OCH₃ | OCH₃ | 183–186 |
| Q-20 | (R₅,R₆ = H) | H | H | 2 | OCH₃ | CH₃ | |
| Q-20 | (R₅ = CH₃, R₆ = H) | H | H | 1 | OCH₃ | CH₃ | |
| Q-20 | (R₅ = H, R₆ = CH₃) | H | H | 1 | OCH₃ | CH₃ | |
| Q-21 | (R₅ = CH₃) | H | H | 1 | OCH₃ | CH₃ | |
| Q-22 | (R₅ = H, R₆ = H) | H | H | 1 | OCH₃ | CH₃ | |
| Q-23 | (R₅ = H, R₆ = CH₃) | H | H | 1 | OCH₃ | CH₃ | |
| Q-24 | (R₅ = CH₃, R₆ = H) | H | H | 1 | OCH₃ | CH₃ | |
| Q-25 | (R₅ = H, R₆ = CH₃) | H | H | 1 | OCH₃ | CH₃ | |
| Q-26 | (R₅ = CH₃, R₆ = CH₃) | H | H | 1 | OCH₃ | OCH₃ | |
| Q-27 | (R₅ = H, R₆ = CH₃) | H | H | 1 | OCH₃ | CH₃ | |
| Q-28 | (R₅ = H, R₆ = H) | H | H | 1 | OCH₃ | OCH₃ | |
| Q-29 | (R₅ = H, R₆ = CH₃) | H | H | 1 | OCH₃ | OCH₃ | |
| Q-30 | (R₅,R₆,R₇ = H) | H | H | 1 | OCH₃ | CH₃ | |
| Q-30 | (R₅,R₆ = H; R₇ = CH₃) | H | H | 1 | OCH₃ | CH₃ | |
| Q-31 | (R₅,R₆,R₇ = CH₃) | H | H | 1 | OCH₃ | CH₃ | |
| Q-31 | (R₅,R₆,R₇ = CH₃) | H | H | 2 | OCH₃ | CH₃ | |
| Q-31 | (R₅,R₆ = H; R₇ = CH₃) | H | H | 1 | OCH₃ | CH₃ | |
| Q-32 | (R₅,R₆,R₇ = H) | H | H | 1 | OCH₃ | CH₃ | |
| Q-33 | (R₅,R₆,R₇ = CH₃) | H | H | 1 | OCH₃ | CH₃ | |
| Q-34 | (R₅,R₆,R₇ = H) | H | H | 1 | OCH₃ | CH₃ | |
| Q-35 | (R₅,R₆,R₇ = H) | H | H | 1 | OCH₃ | CH₃ | |
| Q-35 | (R₅,R₆ = H; R₇ = CH₃) | H | H | 1 | OCH₃ | OCH₃ | |
| Q-36 | (R₅,R₆,R₇ = H) | H | H | 1 | OCH₃ | CH₃ | |
| Q-37 | (R₅,R₆,R₇ = H) | H | H | 1 | OCH₃ | CH₃ | |
| Q-37 | (R₅,R₆,R₇ = H) | H | H | 2 | OCH₃ | CH₃ | |
| Q-38 | (R₅,R₆,R₇ = H) | H | H | 1 | OCH₃ | CH₃ | |
| Q-40 | (R₅ = H) | H | H | 1 | OCH₃ | CH₃ | |
| Q-41 | (R₅ = H) | H | H | 1 | OCH₃ | CH₃ | |
| Q-43 | (R₅ = H) | H | H | 1 | OCH₃ | CH₃ | |
| Q-44 | (R₅ = H) | H | H | 1 | OCH₃ | OCH₃ | |
| Q-45 | (R₅,R₆ = CH₃) | H | H | 1 | OCH₃ | CH₃ | |
| Q-46 | (R₅,R₆ = CH₃) | H | H | 1 | OCH₃ | CH₃ | |
| Q-47 | (R₅,R₆ = CH₃) | H | H | 1 | OCH₃ | CH₃ | |
| Q-48 | (R₅,R₁₁,R₁₂ = CH₃) | H | H | 1 | OCH₃ | CH₃ | |
| Q-48 | (R₅,R₁₁,R₁₂ = CH₃) | H | H | 1 | OCH₃ | OCH₃ | |
| Q-48 | (R₁₁,R₁₂ = OCH₃; R₅ = H) | H | H | 1 | OCH₃ | CH₃ | |
| Q-48 | (R₅ = H; R₁₁,R₁₂ = CH₃) | H | H | 1 | OCH₃ | CH₃ | |
| Q-48 | (R₅,R₁₁,R₁₂ = CH₃) | H | H | 2 | OCH₃ | CH₃ | |
| Q-49 | (R₁₁,R₁₂ = CH₃) | H | H | 1 | OCH₃ | CH₃ | |
| Q-50 | (R₁₁,R₁₂ = CH₃) | H | H | 1 | OCH₃ | CH₃ | |
| Q-51 | (R₅,R₆ = CH₃) | H | H | 1 | OCH₃ | CH₃ | |
| Q-52 | (R₅,R₆ = CH₃) | H | H | 1 | OCH₃ | CH₃ | |
| Q-53 | (R₁₃,R₁₄ = CH₃) | H | H | 1 | OCH₃ | CH₃ | |
| Q-53 | (R₁₃,R₁₄ = OCH₃) | H | H | 1 | OCH₃ | CH₃ | |
| Q-54 | (R₁₃,R₁₄ = CH₃) | H | H | 1 | OCH₃ | CH₃ | |
| Q-54 | (R₁₃,R₁₄ = OCH₃) | H | H | 1 | OCH₃ | CH₃ | |
| Q-13 | (R₈ = SCH₃) | 6-Cl | H | 1 | OCH₃ | CH₃ | |
| Q-13 | (R₈ = SCH₃) | 6-CH₃ | H | 1 | OCH₃ | CH₃ | |
| Q-13 | (R₈ = SCH₃) | 5-CF₃ | H | 1 | CH₃ | OCH₃ | |
| Q-13 | (R₈ = SCH₃) | 5-OCH₃ | H | 1 | CH₃ | OCH₃ | |
| Q-13 | (R₈ = SCH₃) | 5-OCF₂H | H | 1 | OCH₃ | CH₃ | |
| Q-20 | (R₅,R₆ = H) | 6-SCF₂H | H | 1 | OCH₃ | CH₃ | |

TABLE II-continued

| Q | | R₁ | R | n | X | Y | m.p. °C. |
|---|---|---|---|---|---|---|---|
| Q-10 | ($R_8$ = $SCH_3$) | H | H | 1 | $CH_3$ | $OC_2H_5$ | |
| Q-10 | ($R_8$ = $OCH_3$) | H | H | 1 | $OC_2H_5$ | $NHCH_3$ | |
| Q-14 | ($R_9$ = Cl) | H | H | 1 | $OCF_2H$ | $N(OCH_3)CH_3$ | |
| Q-1 | ($R_5,R_6$ = $CH_3$) | H | H | 1 | $OCH_3$ | $N(CH_3)_2$ | |
| Q-10 | ($R_8$ = $SCH_3$) | H | H | 1 | $OCH_3$ | $C_2H_5$ | |
| Q-2 | ($R_5,R_6$ = $CH_3$) | H | H | 1 | $OCH_3$ | $SCH_3$ | |
| Q-3 | ($R_5$ = $CH_3$) | H | H | 1 | $OCH_3$ | $OCH_2CH=CH_2$ | |
| Q-10 | ($R_8$ = $SCH_3$) | H | H | 1 | $CH_3$ | $CH(OCH_3)_2$ | |
| Q-9 | ($R_5,R_6,R_7$ = H) | H | H | 1 | $OCH_2CF_3$ | $CH_3$ | |
| Q-10 | ($R_8$= $SCH_3$) | H | H | 1 | $OCH_2CF_3$ | $OCH_3$ | |
| Q-10 | ($R_8$= $OCH_3$) | H | H | 1 | $OCH_3$ | $C(CH_3)(OCH_3)_2$ | |
| Q-24 | ($R_5,R_6$=$CH_3$) | H | H | 1 | $OCH_3$ | cyclopropyl (CH<CH₂,CH₂>) | |
| Q-10 | ($R_8$ = $OCH_3$) | H | H | 1 | $OCH_3$ | cyclopropyl (CH<CH₂,CH₂>) | |
| Q-51 | ($R_5,R_6$= $CH_3$) | H | H | 2 | $OCH_3$ | $CH_3$ | |
| Q-13 | ($R_8$ = $SCH_2CH=CH_2$) | H | H | 1 | $CH_3$ | $OCH_3$ | |
| Q-13 | ($R_8$ = $SCH_2CH=CH_2$) | H | H | 1 | $OCH_3$ | $OCH_3$ | |
| Q-13 | ($R_8$ = $SCH_2CH=CN$) | H | H | 1 | $CH_3$ | $OCH_3$ | |
| Q-13 | ($R_8$ = $SCH_2CN$) | H | H | 1 | $OCH_3$ | $OCH_3$ | |
| Q-10 | ($R_8$ = $OCH_3$) | H | H | 1 | $OCH_2CH_2F$ | $CH_3$ | |
| Q-10 | ($R_8$ = $SCH_3$) | H | H | 1 | $OCH_2CH_2F$ | $OCH_3$ | |
| Q-20 | ($R_5,R_6$ = H) | H | H | 1 | $OC_2H_5$ | $NHCH_3$ | |
| Q-13 | ($R_8$ = SH) | H | H | 1 | $OCH_3$ | $CH_3$ | |
| Q-13 | ($R_8$ = SH) | H | H | 1 | $OCH_3$ | $OCH_3$ | |

TABLE III

| Q | | R | R₁ | N | X₁ | Y₁ | m.p. °C. |
|---|---|---|---|---|---|---|---|
| Q-1 | ($R_5,R_6$ = H) | H | H | 1 | $CH_3$ | O | |
| Q-2 | ($R_5,R_6$ = H) | H | H | 1 | $CH_3$ | O | |
| Q-3 | ($R_5$ = H) | H | H | 1 | $CH_3$ | O | |
| Q-9 | ($R_5,R_6,R_7$ = H) | H | H | 1 | $CH_3$ | O | |
| Q-9 | ($R_5,R_6,R_7$ = H) | H | H | 2 | $CH_3$ | O | |
| Q-13 | ($R_8$ = $SCH_3$) | H | H | 1 | $CH_3$ | O | |
| Q-13 | ($R_8$ = $SCH_3$) | H | H | 1 | $OCH_3$ | O | |
| Q-13 | ($R_8$ = $SCH_3$) | H | H | 1 | $OC_2H_5$ | O | |
| Q-13 | ($R_8$ = $SCH_3$) | H | H | 1 | $OCF_2H$ | O | |
| Q-13 | ($R_8$ = $SCH_3$) | H | H | 1 | $CH_3$ | $CH_2$ | |
| Q-13 | ($R_8$ = $SCH_3$) | H | H | 1 | $OCH_3$ | $CH_2$ | |
| Q-10 | ($R_8$ = $SCH_3$) | H | H | 2 | $CH_3$ | O | |
| Q-10 | ($R_8$ = $CH_3$) | H | H | 1 | $CH_3$ | O | |
| Q-10 | ($R_8$ = $CH_3$) | H | H | 1 | $OCH_3$ | O | |
| Q-11 | ($R_5$ = H) | H | H | 1 | $CH_3$ | O | |
| Q-12 | ($R_5$ = $CH_3$) | H | H | 1 | $OCH_3$ | O | |
| Q-14 | ($R_9$ = Cl) | H | H | 1 | $CH_3$ | O | |
| Q-20 | ($R_5,R_6$ = H) | H | H | 1 | $CH_3$ | O | |
| Q-20 | ($R_5,R_6$ = H) | H | H | 2 | $CH_3$ | O | |
| Q-24 | ($R_5,R_6$ = H) | H | H | 1 | $CH_3$ | O | |
| Q-48 | ($R_5,R_{11},R_{12}$ = H) | H | H | 1 | $CH_3$ | O | |

TABLE III-continued

| Q | | R | R₁ | N | X₁ | Y₁ | m.p. °C. |
|---|---|---|---|---|---|---|---|
| Q-10 | ($R_8$ = H) | H | H | 1 | $CH_3$ | O | |

TABLE IV

| Q | | R | R₁ | n | X₁ | m.p. °C. |
|---|---|---|---|---|---|---|
| Q-1 | ($R_5,R_6$ = H) | H | H | 1 | $CH_3$ | |
| Q-2 | ($R_5,R_6$ = H) | H | H | 1 | $OCH_3$ | |
| Q-3 | ($R_5$ = H) | H | H | 1 | $CH_3$ | |
| Q-9 | ($R_5,R_6,R_7$ = H) | H | H | 1 | $CH_3$ | |
| Q-9 | ($R_5,R_6,R_7$ = H) | H | H | 2 | $OCH_3$ | |

TABLE IV-continued

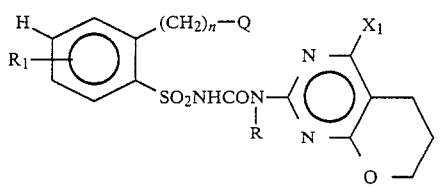

| Q | | R | $R_1$ | n | $X_1$ | m.p. °C. |
|---|---|---|---|---|---|---|
| Q-10 | ($R_8 = C_2H_5$) | H | H | 1 | $CH_3$ | |
| Q-13 | ($R_8 = SCH_3$) | H | H | 1 | $OCH_3$ | |
| Q-10 | ($R_8 = H$) | H | H | 1 | $OC_2H_5$ | |
| Q-10 | ($R_8 = H$) | H | H | 1 | $OCF_2H$ | |
| Q-10 | ($R_8 = SCH_3$) | H | H | 2 | $CH_3$ | |
| Q-10 | ($R_8 = CH_3$) | H | H | 1 | $OCH_3$ | |
| Q-10 | ($R_8 = H$) | H | H | 1 | $CH_3$ | |
| Q-11 | ($R_5 = H$) | H | H | 1 | $CH_3$ | |
| Q-12 | ($R_5 = CH_3$) | H | H | 1 | $OCH_3$ | |
| Q-14 | ($R_9 = Cl$) | H | H | 1 | $CH_3$ | |
| Q-20 | ($R_5, R_6 = H$) | H | H | 1 | $CH_3$ | |
| Q-20 | ($R_5, R_6 = H$) | H | H | 2 | $OCH_3$ | |
| Q-24 | ($R_5, R_6 = H$) | H | H | 1 | $OCH_3$ | |
| Q-48 | ($R_5, R_{11}, R_{12} = H$) | H | H | 1 | $CH_3$ | |
| Q-10 | ($R_8 = H$) | H | H | 1 | $CH_3$ | |

TABLE V

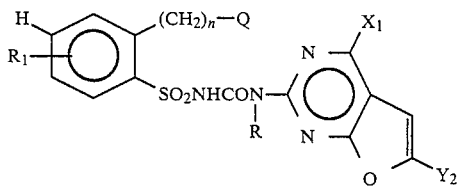

| Q | | R | $R_1$ | n | $X_1$ | $Y_2$ | m.p. °C. |
|---|---|---|---|---|---|---|---|
| Q-1 | ($R_5, R_6 = H$) | H | H | 1 | $CH_3$ | $CH_3$ | |
| Q-2 | ($R_5, R_6 = H$) | H | H | 1 | $CH_3$ | $CH_3$ | |
| Q-3 | ($R_5 = H$) | H | H | 1 | $CH_3$ | H | |
| Q-9 | ($R_5, R_6, R_7 = H$) | H | H | 1 | $CH_3$ | $CH_3$ | |
| Q-9 | ($R_5, R_6, R_7 = H$) | H | H | 2 | $OCH_3$ | $CH_3$ | |
| Q-13 | ($R_8 = SCH_3$) | H | H | 1 | $CH_3$ | $CH_3$ | |
| Q-13 | ($R_8 = SCH_3$) | H | H | 1 | $OCH_3$ | $CH_3$ | |
| Q-10 | ($R_8 = H$) | H | H | 1 | $OC_2H_5$ | $CH_3$ | |
| Q-10 | ($R_8 = CH_3$) | H | H | 1 | $OCF_2H$ | $CH_3$ | |
| Q-10 | ($R_8 = H$) | H | H | 1 | $CH_3$ | H | |
| Q-10 | ($R_8 = H$) | H | H | 2 | $CH_3$ | $CH_3$ | |
| Q-11 | ($R_5 = H$) | H | H | 1 | $CH_3$ | $CH_3$ | |
| Q-12 | ($R_5 = CH_3$) | H | H | 1 | $CH_3$ | $CH_3$ | |
| Q-14 | ($R_9 = Cl$) | H | H | 1 | $OCH_3$ | $CH_3$ | |
| Q-20 | ($R_5, R_6 = H$) | H | H | 1 | $CH_3$ | $CH_3$ | |
| Q-20 | ($R_5, R_6 = H$) | H | H | 2 | $OCH_3$ | $CH_3$ | |
| Q-24 | ($R_5, R_6 = H$) | H | H | 1 | $CH_3$ | $CH_3$ | |
| Q-48 | ($R_5, R_{11}, R_{12} = H$) | H | H | 1 | $CH_3$ | $CH_3$ | |
| Q-39 | ($R_5 = H$) | H | H | 1 | $CH_3$ | $CH_3$ | |
| Q-39 | ($R_5 = CH_3$) | H | H | 1 | $CH_3$ | $CH_3$ | |
| Q-42 | ($R_5 = H$) | H | H | 1 | $CH_3$ | $CH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations. broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE VI

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers"., 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates: solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 1477ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat No. 3,235,361, Feb. 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A Evans, "Weed control Handbook", 5th Ed., Blackwell Scientific Publications, Oxford, 1968, pp. 101-103.

In the following examples, all parts are by weight unless otherwise indicated.

EXAMPLE 9

Wettable Powder

N-[(4,6-dimethoxypyrimidin-2-yl)aminocarbonyl]2-(5-methylthio-1,3,4-thiadiazol-2-ylmethyl)benzenesulfonamide:) 80%
- sodium alkylnaphthalenesulfonate: 2%
- sodium ligninsulfonate: 2%
- synthetic amorphous silica: 3%
- kaolinite: 13%

The ingredients are blended, hammer-milled until all the solids are essentially under 50 microns, reblended, and packaged.

EXAMPLE 10

Wettable Powder

N-[(4,6-dimethoxypyrimidin-2-yl)aminocarbonyl]-2,(5-methylthio-1,3,4-thiadiazol-2-ylmethyl)benzenesulfonamide: 50%
- sodium alkylnaphthalenesulfonate: 2%
- low viscosity methyl cellulose: 2%
- diatomaceous earth: 46%

The ingredients are blended, coarsely hammermilled and then air-milled to produce particles essentially all below 10 microns in diameter. The product is reblended before packaging.

EXAMPLE 11

Granule

Wettable Powder of Example 10: 5%
- attapulgite granules: (U.S.S. 20-40 mesh; 0.84-0.42 mm): 95%

A slurry of wettable powder containing 25% solids is sprayed on the surface of attapulgite granules in a double-cone blender. The granules are dried and packaged.

EXAMPLE 12

Extruded Pellet

N[(4,6-dimethoxypyrimidin-2-yl)aminocarbonyl]-2-(5-methylthio-1,3,4-thiadiazol-2-ylmethyl)benzenesulfonamide: 25%
- anhydrous sodium sulfate: 10%
- crude calcium ligninsulfonate: 5%
- sodium alkylnaphthalenesulfonate: 1%
- calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.Ser. No. 20 sieve (0.84 mm openings). The granules held on a U.S.Ser. No. 40 sieve (0.42 mm openings) may be packaged for use and the fines recycled.

EXAMPLE 13

Low Strength Granule

N-[(4,6-dimethoxypyrimidin-2-yl)aminocarbonyl]-2-(5-methylthio-1,3,4-thiadiazol-2-ylmethyl)benzenesulfonamide: 0.1%
- attapulgite granules (U.S.S. 20-40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

Granule

N-[(4,6-dimethoxypyrimidin-2-yl)aminocarbonyl]-2-(5-methylthio-1,3,4-thiadiazol-2-ylmethyl)benzenesulfonamide: 80%
- wetting agent: 1%
- crude ligninsulfonate salt (containing 5-20% of the natural sugars): 10%
- attapulgite clay: 9%

The ingredients are blended and milled to pass through a 100 mesh screen. This material is then added to a fluid bed granulator, the air flow is adjusted tp gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 15

High Strength Concentrate

N-[(4,6-dimethoxypyrimidin-2-yl)aminocarbonyl]-2-(5-methylthio-1,3,4-thiadiazol-2-ylmethyl)benzenesulfonamide: 99%
- silica aerogel: 0.5%
- synthetic amorphous silica: 0.5%

The ingredients are blended and ground in a hammer-mill to produce a material essentially all passing a U.S.Ser. No. 50 screen (0.3 mm opening). The concentrate may be formulated further if necessary.

EXAMPLE 16

Wettable Powder

N-[(4,6-dimethoxypyrimidin-2-yl)aminocarbonyl]-2-(5-methylthio-1,3,4-thiadiazol-2-ylmethyl)benzenesulfonamide: 90%
- dioctyl sodium sulfosuccinate: 0.1%
- synthetic fine silica: 9.9%

The ingredients are blended and ground in a hammer-mill to produce particles essentially all below 100 microns. The material is sifted through a U.S.Ser. No. 50 screen and then packaged.

EXAMPLE 17

Wettable Powder

N-[(4,6-dimethoxypyrimidin-2-yl)aminocarbonyl]-2-(5-methylthio-1,3,4-thiadiazol-2-ylmethyl)benzenesulfonamide: 40%
- sodium ligninsulfonate: 20%
- montmorillonite clay: 40%

The ingredients are thoroughly blended, coarsely hammer-milled and then air-milled to produce particles essentially all below 10 microns in size. The material is reblended and then packaged.

EXAMPLE 18

Low Strength Granule

N-[(4,6-dimethoxypyrimidin-2-yl)aminocarbonyl]-2-(5-methylthio-1,3,4-thiadiazol-2-ylmethyl)benzenesulfonamide: 1%
 N,N-dimethylformamide: 9%
 attapulgite granules (U.S.S 20-40 sieve:) 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 19

Aqueous Suspension

N-[(4,6-dimethoxypyrimidin-2-yl)aminocarbonyl]-2-(5-methylthio-1,3,4-thiadiazol-2-ylmethyl)benzenesulfonamide: 40%
 polyacrylic acid thickener: 0.3%
 didecylphenol polyethylene glycol ether: 0.5%
 disodium phosphate: 1%
 monosodium phosphate: 0.5%
 polyvinyl alcohol: 1.0%
 water: 56.7%

The ingredients are blended and ground together in a sand mill to produce particles essentially all under 5 microns in size.

EXAMPLE 20

Solution

N-[(4,6-dimethoxypyrimidin-2-yl)aminocarbonyl]-2-(5-methylthio-1,3,4-thiadiazol-2-ylmethyl)benzenesulfonamide, sodium salt: 5%
 water: 95%

The salt is added directly to the water with stirring to produce the solution, which may then be packaged for used.

EXAMPLE 21

Oil Suspension

N-[(4,6-dimethoxypyrimidin-2-yl)aminocarbonyl]-2-(5-methylthio-1,3,4-thiadiazol-2-ylmethyl)benzenesulfonamide: 35%
 blend of polyalcohol carboxylic esters and oil soluble petroleum sulfonates: 6%
 xylene: 59%

The ingredients are combined and ground together in a sand mill to produce particles essentially all below 5 microns. The product can be used directly, extended with oils, or emulsified in water.

EXAMPLE 22

Dust

N-[(4,6-dimethoxypyrimidin-2-yl)aminocarbonyl]-2-(5-methylthio-1,3,4-thiadiazol-2-ylmethyl)benzenesulfonamide: 10%
 attapulgite: 10%
 Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

Test results indicate that the compounds of the present invention are highly active preemergent or postemergent herbicides or plant growth regulators. Many of them have utility for broad-spectrum pre-and/or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as wheat. Alternatively, the subject compounds are useful to modify plant growth.

The rates of application for the compounds of the invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate and bipyridylium types.

The herbicidal properties of the subject compounds were discovered in a number of greenhouse tests. The test procedures and results follow.

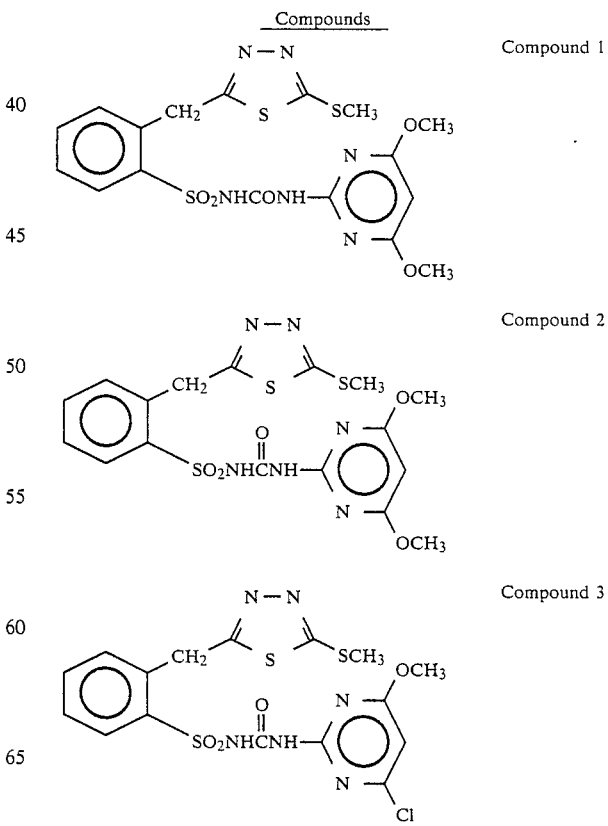

-continued
Compounds

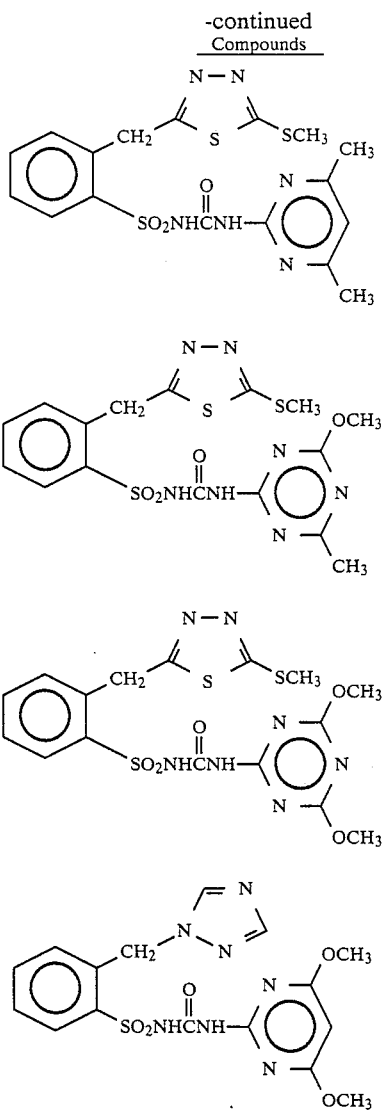

Compound 4
Compound 5
Compound 6
Compound 7

Test A

Seeds of crabgrass (Digitaria sp.), barnyard-grass Echinochloa crusgalli), wild oats (Avena fatua), sicklepod (Cassia obtusifolia), velvetleaf (Abutilon theophrasti), cheatgrass (Bromus secalinus), morninglory (Ipomoea spp.), cocklebur (Xanthium pensylvanicum), sorghum, corn, soybean, sugarbeet, cotton, rice, wheat and purple nutsedge (Cyperus rotundus) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=cholorosis/necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

TABLE A

|  | Cmpd. 1 | Cmpd. 2 | Cmpd. 3 | Cmpd. 4 |
|---|---|---|---|---|
| Rate kg/ha | .05 | .05 | .05 | .05 |
| POST-EMERGENCE |  |  |  |  |
| Morningglory | 3H | 2C,5G | 2C | 1H |
| Cocklebur | 5C,9H | 2C,9H | 3G | 1C |
| Velvet leaf | — | 2G | 0 | 0 |
| Sicklepod | 2C,3G | — | — | — |
| Nutsedge | 5G | 0 | 0 | 0 |
| Crabgrass | 0 | 0 | 0 | 0 |
| Barnyardgrass | 3C,9H | 3C,8H | 2C,8H | 2C,5H |
| Cheatgrass | 2C,6G | 2C,8G | 0 | 4G |
| Wild Oats | 0 | 0 | 0 | 0 |
| Wheat | 0 | 0 | 0 | 0 |
| Corn | 4C,9H | 3H | 0 | 0 |
| Soybean | 5C,9G | 4C,9G | 1H | 2C,7G |
| Rice | 8G | 2H | 4G | 5G |
| Sorghum | 3C,8H | 2C,4G | 2C | 2C,5G |
| Sugar beet | 9C | 5C,9H | 4G | 3C,3H |
| Cotton | 4C,8H | 4C,5G | 0 | 0 |
| PRE-EMERGENCE |  |  |  |  |
| Morningglory | 10E | 6H | 0 | 0 |
| Cocklebur | 3H | 1C | 0 | 0 |
| Velvet leaf | — | 0 | 0 | 0 |
| Sicklepod | 0 | — | — | — |
| Nutsedge | 0 | 0 | 0 | 0 |
| Crabgrass | 0 | 0 | 0 | 0 |
| Barnyardgrass | 2C | 0 | 0 | 0 |
| Wild Oats | 0 | 0 | 0 | 0 |
| Wheat | 0 | 0 | 0 | 0 |
| Corn | 3C,8H | 2G | 1C | 0 |
| Soybean | 2C,2H | 3G | 0 | 0 |
| Rice | 4C,8G | 2G | 5G | 0 |
| Sorghum | 3C,8H | 2C,4G | 2C,5G | 0 |
| Sugar beet | 5G | 3C,4G | 0 | 0 |
| Cotton | 6G | 2C | 0 | 0 |
| Cheatgrass | 4C,8G | 0 | 0 | 0 |

|  | Cmpd. 5 | Cmpd. 6 | Cmpd. 7 |
|---|---|---|---|
| Rate kg/ha | .05 | .05 | .05 |
| POST-EMERGENCE |  |  |  |
| Morningglory | 2C | 2C | 3C,6G |
| Cocklebur | 1C | 2G | 5C,9G |
| Velvet leaf | 0 | 1C | 10C |
| Sicklepod | — | — | — |
| Nutsedge | 0 | 0 | 4C,9G |
| Crabgrass | 0 | 0 | 3G |
| Barnyardgrass | 0 | 0 | 3C,8H |
| Cheatgrass | 0 | 0 | 2C,8G |
| Wild Oats | 0 | 0 | 0 |
| Wheat | 0 | 0 | 0 |
| Corn | 0 | 0 | 3H |
| Soybean | 0 | 1H | 4C,9G |
| Rice | 0 | 0 | 3G |
| Sorghum | 0 | 0 | 2C,9H |
| Sugar beet | 2C,7H | 3H | 9C |
| Cotton | 1C | 0 | 4C,8G |
| PRE-EMERGENCE |  |  |  |
| Morningglory | 0 | 0 | 5G |
| Cocklebur | 0 | 0 | 0 |
| Velvet leaf | 0 | 0 | 5G |
| Sicklepod | — | — | — |
| Nutsedge | 0 | 0 | 4G |
| Crabgrass | 6G | 0 | 0 |
| Barnyardgrass | 0 | 0 | 3G |
| Cheatgrass | 0 | 0 | 0 |
| Wild Oats | 0 | 0 | 2G |
| Wheat | 0 | 0 | 2G |
| Corn | 0 | 0 | 5G |
| Soybean | 0 | 0 | 2G |
| Rice | 0 | 0 | 0 |
| Sorghum | 0 | 0 | 2G |
| Sugar beet | 0 | 0 | 5G |

TABLE A-continued
| Cotton | 0 | 0 | 2G |
|---|---|---|---|
What is claimed is:
1. Compounds of the formula:
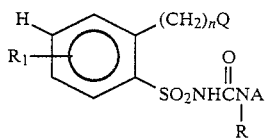
wherein
R is H or CH$_3$;
R$_1$ is H, F, Cl, Br, CH$_3$, CF$_3$, OCH$_3$, SCH$_3$, OCHF$_2$ and SCHF$_2$;
n is 1 or 2;
Q is
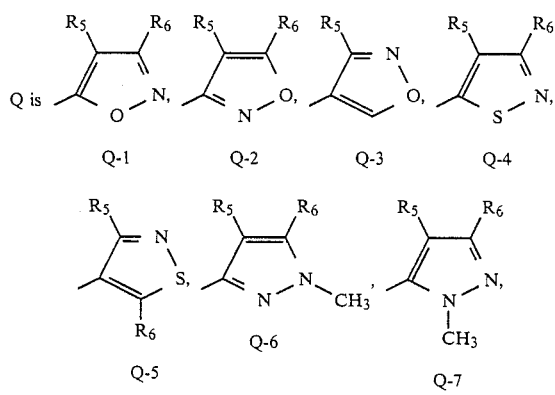
Q-1, Q-2, Q-3, Q-4
Q-5, Q-6, Q-7
Q-8, Q-9, Q-10
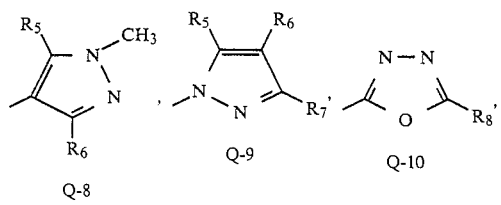
Q-13, Q-14, Q-17
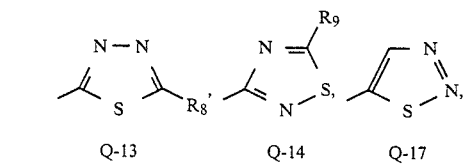
Q-18, Q-19, Q-20
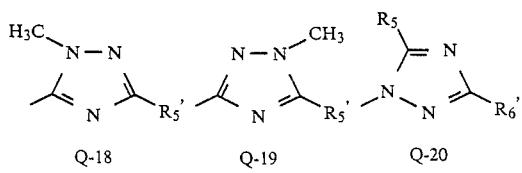
Q-22, Q-23, Q-24
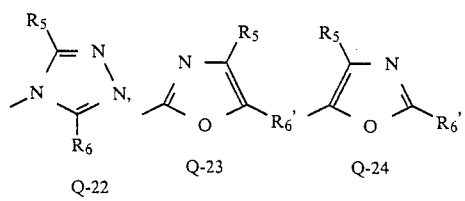
-continued
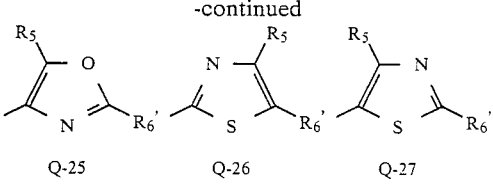
Q-25, Q-26, Q-27
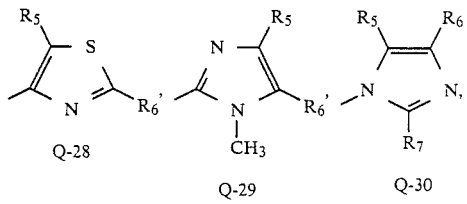
Q-28, Q-29, Q-30
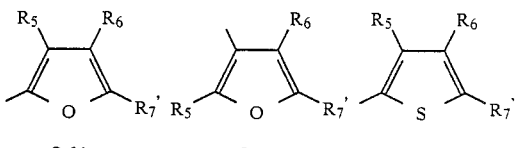
Q-31, Q-32, Q-33
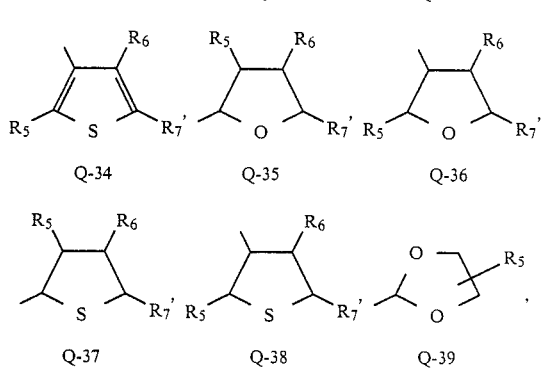
Q-34, Q-35, Q-36
Q-37, Q-38, Q-39
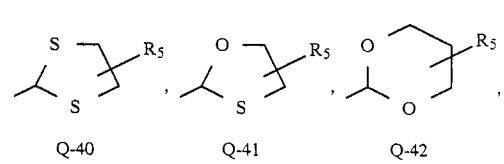
Q-40, Q-41, Q-42
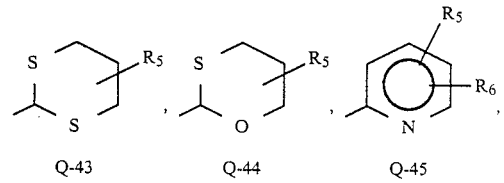
Q-43, Q-44, Q-45
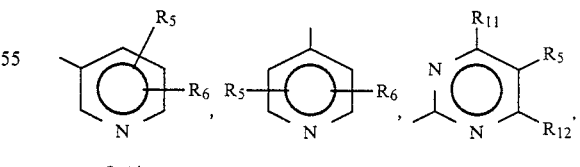
Q-46, Q-47, Q-48
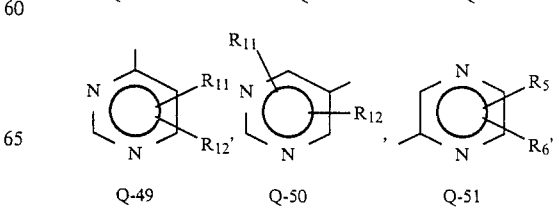
Q-49, Q-50, Q-51

-continued

Q-52, Q-53, Q-54

$R_5$, $R_6$, $R_7$ and $R_{10}$ are independently H or $CH_3$;
$R_8$ is H, $CH_3$, $CH_2CH_3$, SH, $SCH_3$, $SCH_2CH_3$, $OCH_3$, $OCH_2CH_3$, $SCF_2H$, $SCH_2CH=CH_2$ or $SCH_2CN$;
$R_9$ is H or Cl;
$R_{11}$ and $R_{12}$ are independently H, $CH_3$ or $OCH_3$; and
$R_{13}$ and $R_{14}$ are independently $CH_3$ or $OCH_3$;

A is

X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$ or $CF_3$;
Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCH_2CH_2OCH_3$, $CH_2SCH_3$,

, $OCF_2H$, $SCF_2H$ or cyclopropyl;
m is 2 or 3;
$L_1$ and $L_2$ are independently O or S;
$R_2$ is H or $CH_3$;
$R_3$ and $R_4$ are independently $C_1$–$C_2$ alkyl;
Z is CH;
provided that
(a) when X is Cl, F, Br or I, then Y is $OCH_3$, $OC_2H_5$, $N(OCH_3)CH_3$, $NHCH_3$, $N(CH_3)_2$ or $OF_2H$;
(b) when Q is Q-1, Q-2, Q-4, Q-5, Q-6, Q-8, Q-23, Q-24, Q-25, Q-26, Q-27, Q-28, Q-29, Q-45, Q-46, Q-47, Q-51 or Q-52, then one of $R_5$ or $R_6$ is other than H;
(c) when Q is Q-10 or Q-13, then $R_8$ is other than H, $CH_3$ or $CH_2CH_3$;
(d) when Q is Q-14, then $R_9$ is other than H;
(e) when Q is Q-3, Q-18 or Q-19, then $R_5$ is $CH_3$;
(f) when Q is Q-31 or Q-33, then one of $R_5$, $R_6$ or $R_7$ is other than H;
(g) when Q is Q-48, then one of $R_5$, $R_{11}$ or $R_{12}$ is other than H;
(h) when Q is Q-49 or Q-50, then one of $R_{11}$ or $R_{12}$ is other than H;
(i) when Q is Q-53 or Q-54, then one of $R_{13}$ and $R_{14}$ is other than H;

and their agriculturally suitable salts.

2. Compounds of claim 1 wherein R is H.

3. Compounds of claim 2 wherein Q is Q-1, Q-2, q-3, Q-6, Q-7, Q-8, QA-9, Q-10, Q-13, Q-14, Q-17, Q-20, Q-23, Q-24, Q-25, Q-26, Q-29, Q-30, Q-31, Q-32, Q-33, Q-34, Q-35, Q-36, Q-37, Q-38, Q-40, Q-41, Q-43, Q-44, Q-45, Q-46, Q-47, Q-48, Q-49, Q-50, Q-51, Q-52, Q-53, Q-54

4. Compounds of claim 3 wherein Y is $CH_3$, $OCJ_3$, $CH_2OCH_3$, $NHCH_3$, $CH_2CH_3$, $CH(OCH_3)_2$, or cyclopropyl.

5. Compounds of claim 4 wherein $R_1$ is H, Cl, $CH_3$, $SCH_3$, or $OCH_3$ and X is $CH_3$, $OCH_3$, Cl, Br, or $OCF_2H$.

6. Compounds of claim 5 wherein n is 2.

7. Compounds of claim 5 wherein Q is Q-1, Q-2, or Q-3.

8. Compounds of claim 5 wherein Q is Q-6, Q-7, Q-8, or Q-9.

9. Compounds of claim 5 wherein Q is Q-10.

10. Compounds of claim 5 wherein Q is Q-13, Q-14, Q-17, or Q-20.

11. Compounds of claim 5 wherein Q is Q-23, Q-24, Q-25, Q-26, Q-29, or Q-30.

12. Compounds of claim 5 wherein Q is Q-31, Q-32, Q-33, or Q-34.

13. Compounds of claim 5 wherein Q is Q-35, Q-36, Q-37, or Q-38.

14. Compounds of claim 5 wherein Q is Q-40, Q-41, Q-43, or Q-44.

15. Compounds of claim 5 wherein Q is Q-45, Q-46, Q-47, Q-48, Q-49, Q-50, Q-51, Q-52, Q-53, or Q-54.

16. The compound of claim 1 which is N-8 (4,6-dimethoxypyrimidin-2-yl)aminocarbonyl]-2-(5-methylthio-1,3,4-thiadiazol-2-ylmethyl)benzenesulfonamide.

17. A composition suitable for controlling the growth of undesired vegetation which comprises an effective amount of a compound of claim 1 and at least one of the following: surfactant, solid or liquid diluent.

18. A composition suitable for controlling the growth of undesired vegetation which comprises an effective amount of a compound of claim 2 and at least one of the following: surfactant, solid or liquid diluent.

19. A composition suitable for controlling the growth of undesired vegetation which comprises an effective amount of a compound of claim 3 and at least one of the following: surfactant, solid or liquid diluent.

20. A composition suitable for controlling the growth of undesired vegetation which comprises an effective amount of a compound of claim 4 and at least one of the following: surfactant, solid or liquid diluent.

21. A composition suitable for controlling the growth of undesired vegetation which comprises an effective amount of a compound of claim 5 and at least one of the following: surfactant, solid or liquid diluent.

22. A composition suitable for controlling the growth of undesired vegetation which comprises an effective amount of a compound of claim 6 and at least one of the following: surfactant, solid or liquid diluent.

23. A composition suitable for controlling the growth of undesired vegetation which comprises an effective amount of a compound of claim 7 and at least one of the following: surfactant, solid or liquid diluent.

24. A composition suitable for controlling the growth of undesired vegetation which comprises an effective amount of a compound of claim 8 and at least one of the following: surfactant, solid or liquid diluent.

25. A composition suitable for controlling the growth of undesired vegetation which comprises an effective amount of a compound of claim 9 and at least one of the following: surfactant, solid or liquid diluent.

26. A composition suitable for controlling the growth of undesired vegetation which comprises an effective amount of a compound of claim 10 and at least one of the following: surfactant, solid or liquid diluent.

27. A composition suitable for controlling the growth of undesired vegetation which comprises an effective amount of a compound of claim 11 and at least one of the following: surfactant, solid or liquid diluent.

28. A composition suitable for controlling the growth of undesired vegetation which comprises an effective amount of a compound of claim 12 and at least one of the following: surfactant, solid or liquid diluent.

29. A composition suitable for controlling the growth of undesired vegetation which comprises an effective amount of a compound of claim 13 and at least one of the following: surfactant, solid or liquid diluent.

30. A composition suitable for controlling the growth of undesired vegetation which comprises an effective amount of a compound of claim 14 and at least one of the following: surfactant, solid or liquid diluent.

31. A composition suitable for controlling the growth of undesired vegetation which comprises an effective amount of a compound of claim 15 and at least one of the following: surfactant, solid or liquid diluent.

32. A composition suitable for controlling the growth of undesired vegetation which comprises an effective amount of a compound of claim 16 and at least one of the following: surfactant, solid or liquid diluent.

33. A method for controlling the growth of undesired vegetation which comprises applying to the locus to be protected an effective amount of a compound of claim 1.

34. A method for controlling the growth of undesired vegetation which comprises applying to the locus to be protected an effective amount of a compound of claim 2.

35. A method for controlling the growth of undesired vegetation which comprises applying to the locus to be protected an effective amount of a compound of claim 3.

36. A method for controlling the growth of undesired vegetation which comprises applying to the locus to be protected an effective amount of a compound of claim 4.

37. A method for controlling the growth of undesired vegetation which comprises applying to the locus to be protected an effective amount of a compound of claim 5.

38. A method for controlling the growth of undesired vegetation which comprises applying to the locus to be protected an effective amount of a compound of claim 6.

39. A method for controlling the growth of undesired vegetation which comprises applying to the locus to be protected an effective amount of a compound of claim 7.

40. A method for controlling the growth of undesired vegetation which comprises applying to the locus to be protected an effective amount of a compound of claim 8.

41. A method for controlling the growth of undesired vegetation which comprises applying to the locus to be protected an effective amount of a compound of claim 9.

42. A method for controlling the growth of undesired vegetation which comprises applying to the locus to be protected an effective amount of a compound of claim 10.

43. A method for controlling the growth of undesired vegetation which comprises applying to the locus to be protected an effective amount of a compound of claim 11.

44. A method for controlling the growth of undesired vegetation which comprises applying to the locus to be protected an effective amount of a compound of claim 12.

45. A method for controlling the growth of undesired vegetation which comprises applying to the locus to be protected an effective amount of a compound of claim 13.

46. A method for controlling the growth of undesired vegetation which comprises applying to the locus to be protected an effective amount of a compound of claim 14.

47. A method for controlling the growth of undesired vegetation which comprises applying to the locus to be protected an effective amount of a compound of claim 15.

48. A method for controlling the growth of undesired vegetation which comprises applying to the locus to be protected an effective amount of a compound of claim 16.

49. Compounds of the formula:

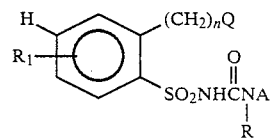

wherein
R is H or $CH_3$;
$R_1$ is H, F, Cl, Br, $Ch_3$, $CF_3$, $OCH_3$, $SCH_3$, $OCHF_2$ or $SCHF_2$;
n is 1 or 2;
Q is

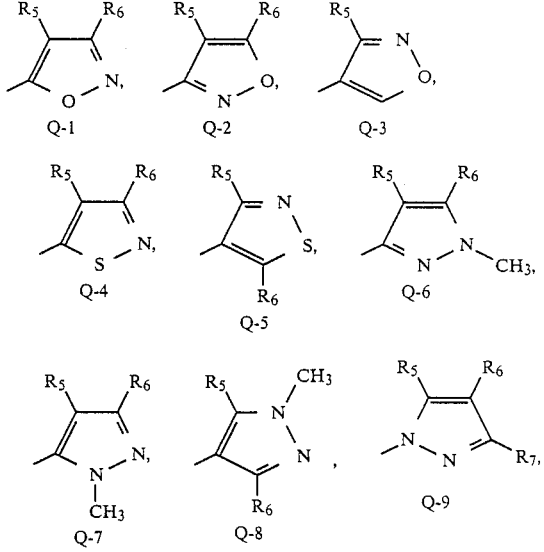

-continued

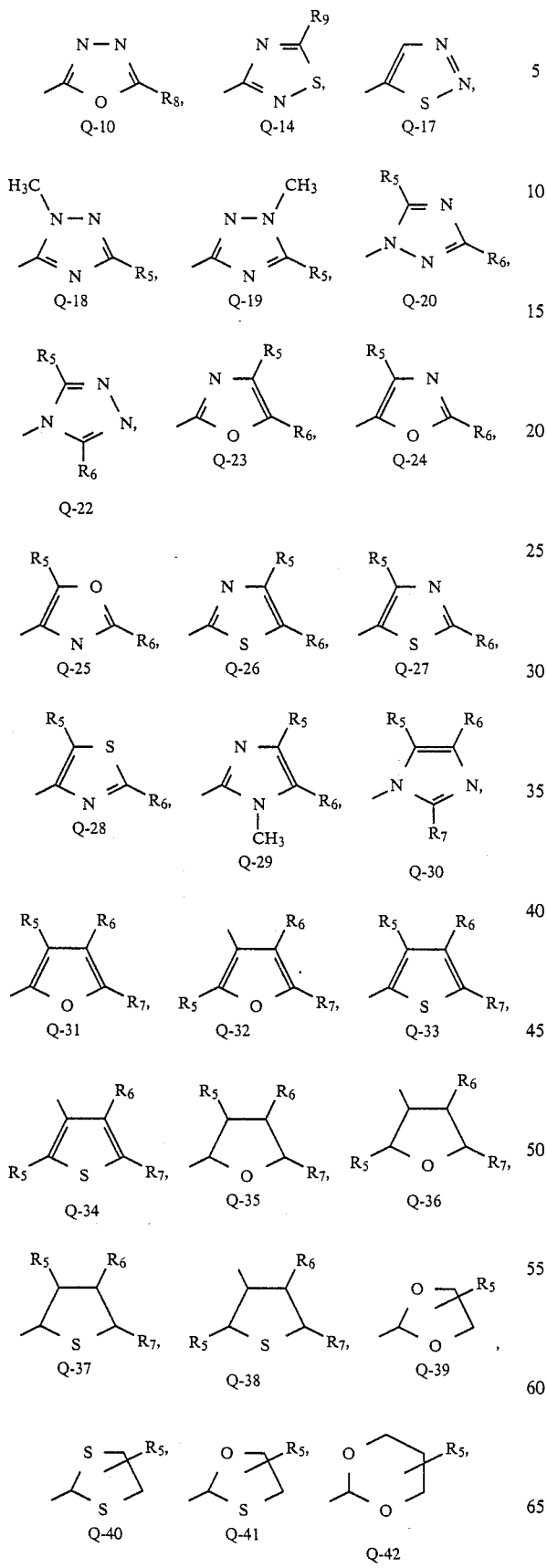

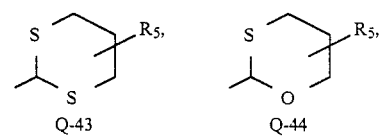

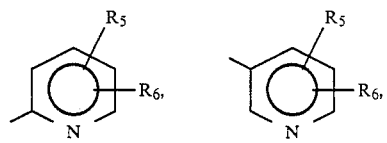

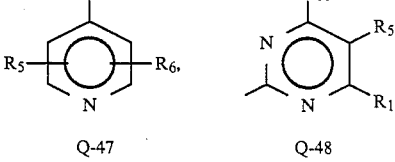

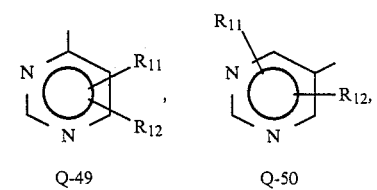

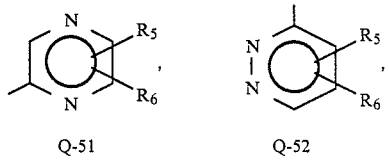

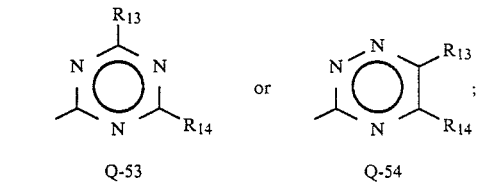

$R_5$, $R_6$, $R_7$ and $R_{10}$ are independently H or $CH_3$;
$R_8$ is H, $CH_3$, $CH_2CH_3$, $SCH_3$, $SCH_2CH_3$, $OCH_3$, $OCH_2CH_3$, $SCF_2H$, $SCH_2CH=CH_2$ or $SCH_2CN$;
$R_9$ *l is H or Cl*;
$R_{11}$ and $R_{12}$ are independently H, $CH_3$ or $OCH_3$; and
$R_{13}$ and $R_{14}$ are independently $CH_3$ or $OCH_3$;

A is 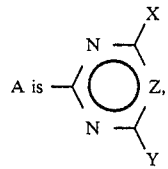

X is $CH_3$, $OCH_3$, $OCH_2CH_3$, Cl, F, BR, I, $OCF_2H$, $CH_2F$, $OCH_2CH_2F$, $OCH_2CHF_2$, $OCH_2CF_3$ or $CF_3$;
Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$,

OCH$_2$CH$_2$OCH$_3$, CH$_2$SCH$_3$, $$-\overset{O}{\overset{\|}{C}}-R_2, \quad -\overset{L_1R_3}{\underset{L_2R_4}{\overset{|}{C}}}-R_2,$$

$$-\overset{L_1}{\underset{R_2}{\overset{|}{C}}}\overset{L_1}{\underset{L_2}{\diagup}}(CH_2)_m\overset{L_1}{\underset{L_2}{\diagdown}}\overset{CH_3}{\underset{CH_2}{\overset{|}{CR_2}}}, \quad OCF_2H, SCF_2H$$

m is 2 or 3;
L$_1$ and L$_2$ are independently O or S;
R$_2$ is H or CH$_3$;
R$_3$ and R$_4$ are independently C$_1$–C$_2$ alkyl;
Z is CH.
provided that (a) when X is Cl, F, Br or I, then Y is OCH$_3$, OC$_2$H$_5$, N(OCH$_3$)CH$_3$, NHCH$_3$, N(CH$_3$)$_2$ or OCF$_2$H;
(b) when Q is Q-1, Q-2, Q-4, Q-5, Q-6, Q-8, Q-23, Q-24, Q-25, Q-26, Q-27, Q-28, Q-29, Q-45, Q-46, Q-47, Q-51 or Q-52, then one of R$_5$ or R$_6$ is other than H;
(c) when Q is Q-10, then R$_8$ is other than H, CH$_3$ or CH$_2$CH$_3$;
(d) when Q is Q-14, then R$_9$ is other than H;
(e) when Q is Q-3, or Q-19, then R$_5$ is CH$_3$;
(f) when Q is Q-31 or Q-33, then one of R$_5$, R$_6$ or R$_7$ is other than H;
(g) when q is Q-48, then one of R$_5$, R$_{11}$ or R$_{12}$ is other than H;
(h) when Q is Q-49 or Q-50, then one of R$_{11}$ or R$_{12}$ is other than H;
(i) when Q is Q-53 or Q-54, then one of R$_{13}$ and R$_{14}$ is other than H;
and their agriculturally suitable salts.

50. Compounds of the formula:

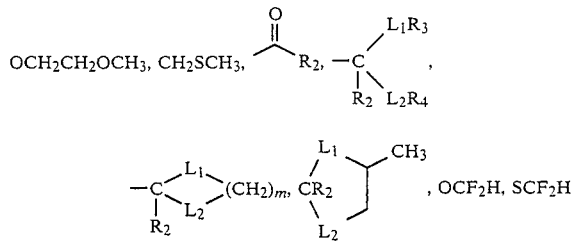

wherein
R is H or CH$_3$;
R$_1$ is H, F, Cl, Br, CH$_3$, CF$_3$, OCH$_3$, SCH$_3$, OCHF$_2$ or SCHF$_2$;
n is 1 or 2;

Q is $$\overset{N-N}{\underset{O}{\diagup\diagdown}}\overset{}{\underset{}{}}\text{SH};$$

A is $$-\overset{N}{\underset{N}{\diagup}}\overset{X}{\underset{Y}{\diagdown}}Z;$$

X is CH$_3$, OCH$_3$, OCH$_2$CH$_3$, Cl, F, Br, I, OCF$_2$H, CH$_2$F, OCH$_2$CH$_2$F, OCH$_2$CHF$_2$, OCH$_2$CF$_3$ or CF$_3$;

Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$,

OCH$_2$CH$_2$OCH$_3$, CH$_2$SCH$_3$, $$-\overset{O}{\overset{\|}{C}}-R_2, \quad -\overset{L_1R_3}{\underset{L_2R_4}{\overset{|}{C}}}-R_2,$$

$$-\overset{L_1}{\underset{R_2}{\overset{|}{C}}}\overset{L_1}{\underset{L_2}{\diagup}}(CH_2)_m\overset{L_1}{\underset{L_2}{\diagdown}}\overset{CH_3}{\underset{CH_2}{\overset{|}{CR_2}}}, \quad OCF_2H, SCF_2H$$

or cyclopropyl;
m is 2 or 3;
L$_1$ and L$_2$ are independently O or S;
R$_2$ is H or CH$_3$;
R$_3$ and R$_4$ are independently C$_1$–C$_2$ alkyl;
Z is CH: provided that when X is Cl, F, Br, or I, then Y is OCH$_3$, OC$_2$H$_5$, N(OCH$_3$)CH$_3$, NHCH$_3$, N(CH$_3$)$_2$ or OCF$_2$H; and their agriculturally suitable salts.

51. Compounds of the formula:

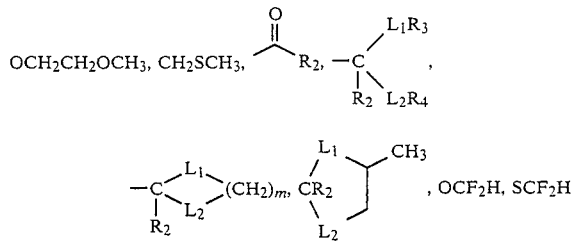

wherein
R is H or CH$_3$;
R$_1$ is H, F, Cl, Br, CH$_3$, CF$_3$, OCH$_3$, SCH$_3$, OCHF$_2$ or SCHF$_2$;
n is 1 or 2;
Q is $$\overset{N-N}{\underset{S}{\diagup\diagdown}}R_8;$$

R$_8$ is SH, SCH$_3$, SCH$_{12}$CH$_3$, OCH$_3$, OCH$_2$CH$_3$, SCF$_2$H, SCH$_2$CH=CH$_2$ or SCH$_2$CN;

A is $$-\overset{N}{\underset{N}{\diagup}}\overset{X}{\underset{Y}{\diagdown}}Z;$$

X is CH$_3$, OCH$_3$, OCH$_2$CH$_3$, Cl, F, Br, I, OCF$_2$H, CH$_2$F, OCH$_2$CH$_2$F, OCH$_2$CHF$_2$, OCH$_2$CF$_3$ or CF$_3$;

Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, Sch$_3$, OCH$_2$CH=CH$_2$, OCH$_2$C≡CH, CH$_2$OCH$_2$CH$_3$,

OCH$_2$CH$_2$OCH$_3$, CH$_2$SCH$_3$, $$-\overset{O}{\overset{\|}{C}}-R_2, \quad -\overset{L_1R_3}{\underset{L_2R_4}{\overset{|}{C}}}-R_2,$$

-continued

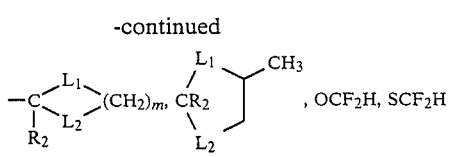, OCF$_2$H, SCF$_2$H or cyclopropyl;

m is 2 or 3;

L$_1$ and L$_2$ are independently O or S;

R$_2$ is H or CH$_3$;

R$_3$ and R$_4$ are independently C$_1$–C$_2$ alkyl;

Z is CH; provided that when X is Cl, F, Br or I, then Y is OCH$_3$, OC$_2$H$_5$, N(OCH$_3$)CH$_3$, NHCH$_3$, N(CH$_3$)$_2$ or OCF$_2$H;

and their agriculturally suitable salts.

52. Compounds of claim 49 wherein Q is Q-9, Q-20, Q-22, Q-30, Q-35, Q-36, Q-37, Q-38, Q-39, Q-40, Q-41, Q-42, Q-43 or Q-44.

53. Compounds of claim 49 wherein R$_8$ is SCH$_3$, SCH$_2$CH$_3$, OCH$_3$, OCH$_2$CH$_3$, SCF$_2$H, SCH$_2$CH=CH$_2$ or SCH$_2$CN.

54. Compounds of claim 49 wherein Q is Q-7, Q-17, Q-18, or Q-32.

* * * * *